(12) United States Patent
Allerton et al.

(10) Patent No.: US 7,576,081 B2
(45) Date of Patent: Aug. 18, 2009

(54) MORPHOLINE DOPAMINE AGONISTS

(75) Inventors: Charlotte Moira Norfor Allerton, Sandwich (GB); Andrew Douglas Baxter, Sandwich (GB); Andrew Simon Cook, Sandwich (GB); David Hepworth, Sandwich (GB); Stephen Kwok-Fung Wong, Guilford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/425,030

(22) Filed: Jun. 19, 2006

(65) Prior Publication Data
US 2006/0235016 A1    Oct. 19, 2006

Related U.S. Application Data

(62) Division of application No. 10/727,168, filed on Dec. 2, 2003, now Pat. No. 7,323,462.

(60) Provisional application No. 60/438,476, filed on Jan. 7, 2003, provisional application No. 60/470,950, filed on May 15, 2003, provisional application No. 60/501,512, filed on Sep. 8, 2003.

(30) Foreign Application Priority Data

| Dec. 10, 2002 | (GB) | ................................. | 0228787.8 |
| Apr. 11, 2003 | (GB) | ................................. | 0308460.5 |
| Jun. 12, 2003 | (GB) | ................................. | 0313606.6 |

(51) Int. Cl.
*A61K 31/5377* (2006.01)
*C07D 413/04* (2006.01)
(52) U.S. Cl. .................. 514/235.2; 544/124
(58) Field of Classification Search .................. None
See application file for complete search history.

(56) References Cited

U.S. PATENT DOCUMENTS 2,503,059 A     4/1950  Miescher et al. ......... 260/309.6

(Continued)

FOREIGN PATENT DOCUMENTS

EP          0463756         1/1992

(Continued)

OTHER PUBLICATIONS

Stocker, et al., NIDA Notes, Research Findings, vol. 14, No. 6 (Mar. 2000).*

(Continued)

*Primary Examiner*—Kamal A Saeed
(74) *Attorney, Agent, or Firm*—Gregg C. Benson; A. Dean Olson

(57) ABSTRACT

The present invention provides for compounds of formula (I), (Ia) and (Ib)

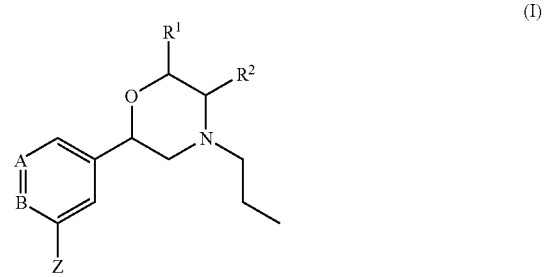

(I)

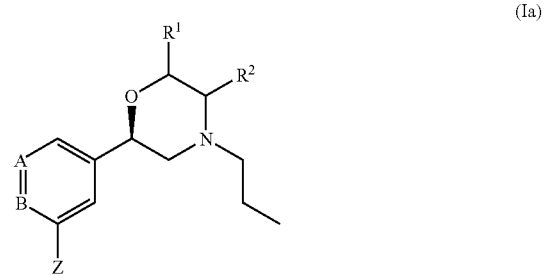

(Ia)

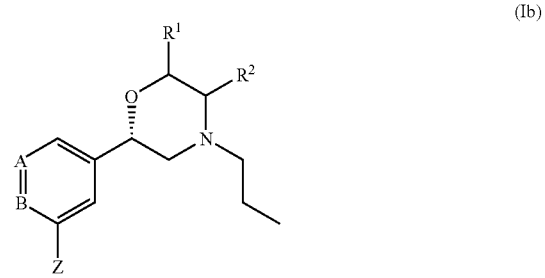

(Ib)

Wherein:
A is selected from C—X and N,
B is selected from C—Y and N,
$R^1$ is selected from H and $(C_1\text{-}C_6)$alkyl,
$R^2$ is selected from H and $(C_1\text{-}C_6)$alkyl,
X is selected from H, HO, $C(O)NH_2$, $NH_2$
Y is selected from H, HO, $NH_2$, Br, Cl and F
Z is selected from H, HO F, $CONH_2$ and CN;
And pharmaceutically acceptable salts, solvates and prodrugs thereof;
With the provisos that:
for a compound of formula (I), (Ia) or (Ib), when A is C—X, B is C—Y, $R^1$ is H or $(C_1\text{-}C_6)$alkyl and $R^2$ is H or $(C_1\text{-}C_6)$alkyl at least one of X, Y and Z must be OH;
for a compound of formula (I), when A is C—X and B is C—Y, Y is H, Z is H, $R^1$ is H and $R^2$ is H, then X cannot be OH;
these compounds are useful as a medicament.

3 Claims, No Drawings

U.S. PATENT DOCUMENTS

| | | | | |
|---|---|---|---|---|
| 2,599,000 | A | 6/1952 | Kerwin et al. | 260/570.7 |
| 3,381,009 | A | 4/1968 | Palazzo et al. | 260/268 |
| 3,511,836 | A | 5/1970 | Hess | 260/256.4 |
| 3,527,761 | A | 9/1970 | Archibald et al. | 260/293 |
| 3,997,666 | A | 12/1976 | Witte et al. | 424/250 |
| 4,026,894 | A | 5/1977 | Winn et al. | 260/256.4 Q |
| 4,188,390 | A | 2/1980 | Campbell | 424/251 |
| 4,252,721 | A | 2/1981 | Silvestrini et al. | 260/243.3 |
| 4,315,007 | A | 2/1982 | Manoury | 424/251 |
| 4,703,063 | A | 10/1987 | Imai et al. | 514/603 |
| 5,077,290 | A | 12/1991 | Fisher et al. | 514/233.2 |
| 5,258,513 | A | 11/1993 | Van Keulen | 544/58.2 |
| 5,348,956 | A | 9/1994 | Van Keulen | 514/232.2 |
| 5,578,322 | A | 11/1996 | Takase et al. | 514/260 |
| 5,698,560 | A | 12/1997 | Onoda et al. | 514/267 |
| 6,037,346 | A | 3/2000 | Doherty et al. | 514/258 |
| 6,297,382 | B1 | 10/2001 | Scott | 546/276.4 |
| 2006/0052435 | A1* | 3/2006 | Van der Graaf et al. | 514/419 |

FOREIGN PATENT DOCUMENTS

| | | |
|---|---|---|
| EP | 0526004 | 7/1992 |
| EP | 0995750 | 4/2000 |
| EP | 0995751 | 4/2000 |
| EP | 1092718 | 4/2001 |
| EP | 1092719 | 4/2001 |
| GB | 851311 | 10/1960 |
| RU | 2095353 | 10/1997 |
| SU | 1154907 | 9/1996 |
| WO | WO9218489 | 10/1962 |
| WO | WO9111172 | 8/1991 |
| WO | WO9306104 | 4/1993 |
| WO | WO9307149 | 4/1993 |
| WO | WO9312095 | 6/1993 |
| WO | WO9400453 | 1/1994 |
| WO | WO9402518 | 2/1994 |
| WO | WO9405661 | 3/1994 |
| WO | WO9519978 | 7/1995 |
| WO | WO9621656 | 7/1996 |
| WO | WO9849166 | 11/1998 |
| WO | WO9855148 | 12/1998 |
| WO | WO9902159 | 1/1999 |
| WO | WO9924433 | 5/1999 |
| WO | WO9930697 | 6/1999 |
| WO | WO9932475 | 7/1999 |
| WO | WO9954333 | 10/1999 |
| WO | WO9954358 | 10/1999 |
| WO | WO9955679 | 11/1999 |
| WO | WO9964002 | 12/1999 |
| WO | WO9964008 | 12/1999 |
| WO | WO0002550 | 1/2000 |
| WO | WO0012075 | 3/2000 |
| WO | WO0024745 | 5/2000 |
| WO | WO0028993 | 5/2000 |
| WO | WO0033825 | 6/2000 |
| WO | WO0058361 | 10/2000 |
| WO | WO0074679 | 12/2000 |
| WO | WO0105401 | 1/2001 |
| WO | WO0113112 | 2/2001 |
| WO | WO0114879 | 3/2001 |
| WO | WO0127112 | 4/2001 |
| WO | WO0127113 | 4/2001 |

OTHER PUBLICATIONS

Morissette et al. Advanced Drug Delivery Reviews, 56, 275-300 (2004).*

Brown, et al. "Designing drugs for the treatment of female sexual dysfunction", Drug Discovery Today, vol. 12, pp. 757-766 (Sep. 2007).*

Berman, et al., "Femal Sexual Dysfunction: Incidence, Pahtophysiology, Evaluation, and Treatment Options", *Urology* 54, pp. 385-391 (1999).

Melman, et al., "The Epidemiology and Pathophysiology of Erectile Dysfunction", *The Journal of Urology* 161, pp. 5-11 (1999).

Gonzalez, et al., "[$^3$H]7-OH-DPAT is Capable of Labeling Dopamine $D_2$ as well as $D_3$ Receptors", *European Journal of Pharmacology* 272, pp. R1-R3 (1995).

Ballard, et al., "Effects of Sildenafil on the Relaxation of Human Corpus Cavenosum Tissue In Vitro and on the Activities of cyclic Nucleotide Phosphodiesterase Isozymes", *The Journal of Urology* 159(6), pp. 2164-2171 (1998).

Rotella, et al., "N-3-Substituted Imidazoquinalinones: Potent and Selective PDE5 Inhibitors as Potential Agents for Treatment of Erectile Dysfunction", *J. Med. Chem.*, 43, pp. 1257-1263 (2000).

Berge, et al., "Pharmaceutical Salts", *Journal of Pharmaceutical Sciences* 66(1), pp. 1-19 (1977).

Taub, et al., "Relationship between Contraction and Relaxation in Human and Rabbit Corpus Cavemosum", *Urology* 42(6), pp. 698-704 (1993).

Leiblum, "Definition and Classification of Female Secual Disorders", *International Journal of Impotence Research* 10(Suppl. 2), pp. S104-S106 (1998).

Goldstein, et al., "Vasculogenic Female Sexual Dysfunction: Vaginal Engorement and Clitoral Erectile Insufficiency Syndromes", *International Journal of Impotence Research* 10(Suppl. 2), pp. S84-S90 (1998).

Park, et al., "Vasculogenic Female Sexual Dysfunction: The Hemodynamic Basis for Vaginal Engorgement Insufficiency and Clitoral Erectile Insufficiency", *International Journal of Impotence Research* 9, pp. 27-37 (1997).

Levin, "VIP, Vagina, Clitoral and Periurethral Glans—an Update on Human Female Genital Arousal", *Exp. Clin. Endocrinol.* 98(2), pp. 61-69 (1991).

Lerner, et al., "A Review of Erectile Dysfunction: New Insights and More Questions", *The Journal of Urology* 149, pp. 1246-1255 (1993).

Feldman, et al., "Impotence and Its Medical and Psychosocial Correlates: Resulst of the Massachusetts Male Aging Study", *The Journal of Urology* 161, pp. 54-61 (1994).

Naylor, "Endogenous Neurotransmitters Mediating Penile Erection", *British Journal of Urology* 81, pp. 424-431 (1996).

Carrier, et al., "Erectile Dysfunction", *Clinical Andrology* 23(4), pp. 773-782 (1994).

Perrone, et al, "Oxygen Derivatives of 3-(3-hydroxyphenyl)-N-n-propylpiperldine", 35, pp. 3045-3049, (1992), *Journal of Med. Chem.*

* cited by examiner

MORPHOLINE DOPAMINE AGONISTS

This is a divisional application of U.S. Non-provisional application Ser. No. 10/727,168, filed on Dec. 23, 2004, which claims priority from U.S. Provisional Application Ser. No. 60/438,476 filed on Jan. 7, 2003; U.S. Provisional Application Ser. No. 60/470,950 tiled on May 15, 2003; U.S Provisional Application Ser. No 60/501,512 filed on Sep. 8, 2003; the United Kingdom Application Serial No. 0228787.8 filed on Dec. 10, 2002, United Kingdom Application Serial No. 0308460.5 filed on Apr. 11, 2003; and United Kingdom Application Serial No. 0313606.6 filed on Jun. 12. 2003.

The present invention relates to a class of dopamine agonists, more particularly a class of agonists that are selective for D3 over D2. These compounds are useful for the treatment and/or prevention of sexual dysfunction, for example female sexual dysfunction (FSD), in particular female sexual arousal disorder (FSAD) and male sexual dysfunction, in particular male erectile dysfunction (MED). Male sexual dysfunction as referred to herein is meant to include ejaculatory disorders such as premature ejaculation, anorgasmia (inability to achieve orgasm) or desire disorders such as hypoactive sexual desire disorder (HSDD; lack of interest in sex). These compounds are also useful in treating neuropsychiatric disorders and neurodegenerative disorders.

The present invention provides for compounds of formula (I), (Ia) and (Ib)

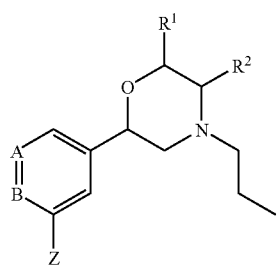

(I)

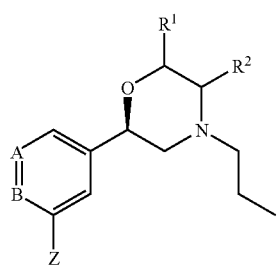

(Ia)

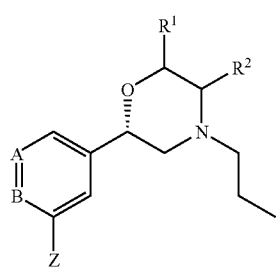

(Ib)

Wherein:
A is selected from C—X and N,
B is selected from C—Y and N,
$R^1$ is selected from H and $(C_1-C_6)$alkyl,
$R^2$ is selected from H and $(C_1-C_6)$alkyl,
X is selected from H, HO, C(O)$NH_2$, $NH_2$
Y is selected from H, HO, $NH_2$, Br, Cl and F
Z is selected from H, HO, F, $CONH_2$ and CN;
And pharmaceutically acceptable salts, solvates and prodrugs thereof;
With the provisos that:
for a compound of formula (I), (Ia) or (Ib), when A is C—X, B is C—Y, $R^1$ is H or $(C_1-C_6)$alkyl and $R^2$ is H or $(C_1-C_6)$alkyl at least one of X, Y and Z must be OH;
for a compound of formula (I), when A is C—X and B is C—Y, Y is H, Z is H, $R^1$ is H and $R^2$ is H, then X cannot be OH.

The pharmaceutically acceptable salts of the compounds of the formula (I) include the acid addition and the base salts thereof.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1-19, 1977.

The pharmaceutically acceptable solvates of the compounds of the formula (I) include the hydrates thereof.

Also included within the present scope of the compounds of the formula (I) are polymorphs thereof.

A compound of the formula (I) contains one or more asymmetric carbon atoms and therefore exists in two or more stereoisomeric forms.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferred compounds of the present invention are compounds of formula (Ia) and (Ib)
Particularly preferred are compounds of formula (Ia)
Preferably A is C—X or N and B is C—Y
More preferably A is N and B is C—Y
More preferably A is C—X and B is C—Y
Preferably $R^1$ is selected from H and $(C_1-C_4)$alkyl.
More preferably $R^1$ is H, methyl and ethyl
Even more preferably $R^1$ is H or methyl.
Most preferably $R^1$ is H.
Preferably $R^2$ is selected from H and $(C_1-C_4)$alkyl.
More preferably $R^2$ is selected from H, methyl and ethyl.
Most preferably $R^2$ is selected from H and methyl.
In a particularly preferred embodiment $R^2$ is H
In a further particularly preferred embodiment $R^2$ is methyl Preferably X is selected from H, OH and NH$_2$
Most preferably X is selected from H and OH.
In a particularly preferred embodiment X is H
In a further particularly preferred embodiment X is OH
Preferably Y is selected from H, NH$_2$, Cl and F
Most preferably Y is selected from H and NH$_2$.
In a particularly preferred embodiment Y is H
In a further particularly preferred embodiment Y is NH$_2$
Preferably Z is selected from H, HO and F.
Most preferably Z is selected from H or HO.
In a particularly preferred embodiment Z is H
In a further particularly preferred embodiment Z is HO
Particularly preferred are compounds (and salts thereof) of the present invention exemplified herein; more preferred are:
R-(−)-3-(4-Propylmorpholin-2-yl)phenol (Example 7A)
S-(+)-3-(4-Propylmorpholin-2-yl)phenol (Example 7B)
R-(−)-3-(4-Propylmorpholin-2-yl)phenol hydrochloride (Example 8)
R-5-(4-Propylmorpholin-2-yl)benzene-1,3-diol (Example 15A)
S-5-(4-Propylmorpholin-2-yl)benzene-1,3-diol (Example 15B)
R-(+)-2-Fluoro-5-(4-propylmorpholin-2-yl)phenol (Example 23A)
S-(−)-2-Fluoro-5-(4-propylmorpholin-2-yl)phenol (Example 23B)
2-Bromo-4-(4-propylmorpholin-2-yl)phenol (Example 30)
2-Hydroxy-5-(4-propylmorpholin-2-yl)benzamide (Example 35)
2-Nitro-4-(4-propylmorpholin-2-yl)phenol (Example 36)
2-Amino-4-(4-propylmorpholin-2-yl)phenol (Example 37)
5-(4-Propylmorpholin-2-yl)pyridin-2-ylamine (Example 44A and 44B)
2-Chloro-5-(4-propyl-morpholin-2-yl)phenol (Example 54)
3-[(5S)-5-methyl-4-propylmorpholin-2-yl]phenol (Example 60)
5-[(2S,5S)-5-methyl-4-propylmorpholin-2-yl]pyridin-2-amine (Example 66)
5-[(2R,5S)-5-methyl-4-propylmorpholin-2-yl]pyridin-2-amine (Example 67)
Most preferred are:
R-(−)-3-(4-Propylmorpholin-2-yl)phenol (Example 7A)
S-(+)-3-(4-Propylmorpholin-2-yl)phenol (Example 7B)
R-(−)-3-(4-Propylmorpholin-2-yl)phenol hydrochloride (Example 8)
R-5-(4-Propylmorpholin-2-yl)benzene-1,3-diol (Example 15A)
S-5-(4-Propylmorpholin-2-yl)benzene-1,3-diol (Example 15B)
R-(+)-2-Fluoro-5-(4-propylmorpholin-2-yl)phenol (Example 23A)
S-(−)-2-Fluoro-5-(4-propylmorpholin-2-yl)phenol (Example 23B)
5-(4-Propylmorpholin-2-yl)pyridin-2-ylamine (Example 44A and 44B)
2-Chloro-5-(4-propyl-morpholin-2-yl)phenol (Example 54)
5-[(2S,5S)-5-methyl-4-propylmorpholin-2-yl]pyridin-2-amine (Example 66)
5-[(2R,5S)-5-methyl-4-propylmorpholin-2-yl]pyridin-2-amine (Example 67)

Compounds of the invention may be prepared, in known manner, in a variety of ways. The routes below illustrate methods of synthesising compounds of formula (I); the skilled man will appreciate that compounds of formula (Ia) and (Ib) may be isolated with appropriate resolution techniques.

Compounds of general formula I where A is C—X, B is C—Y, R$^1$ is H or (C$_1$-C$_6$)alkyl, R$^2$ is H and where X, Y and Z are as described herein may be prepared according to reaction scheme 1.

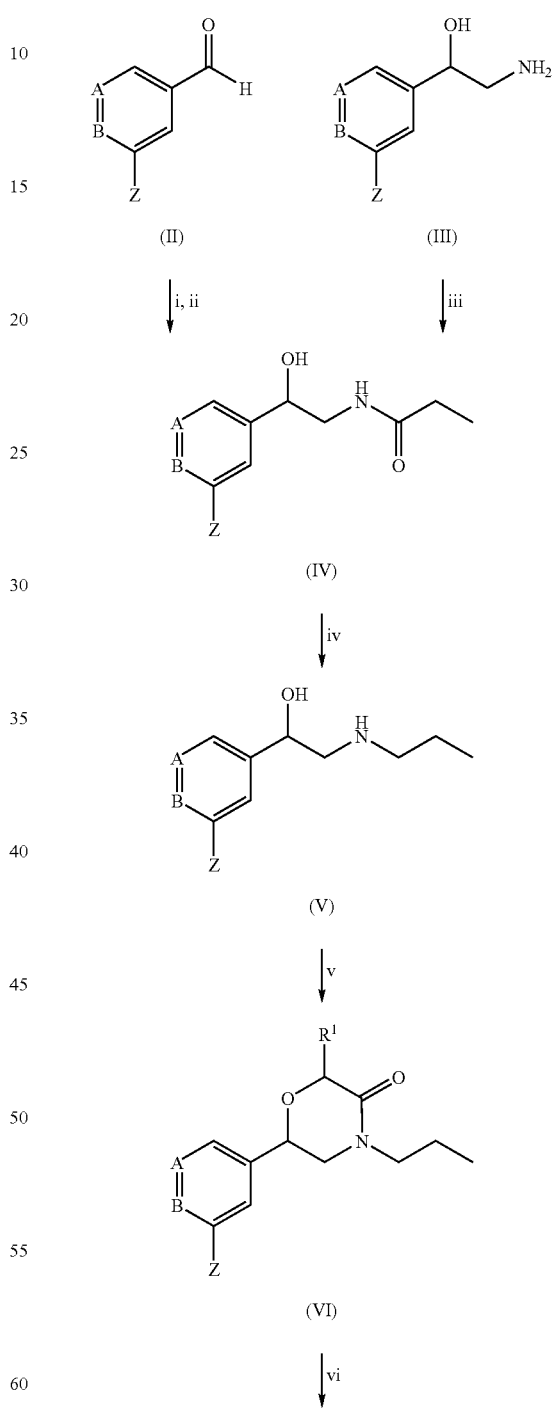

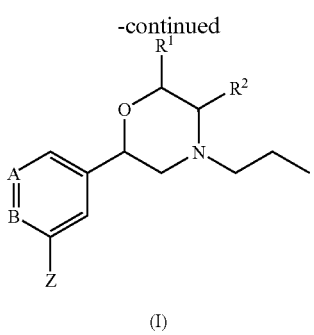

(I)

Compounds of formula (III) may be prepared by reacting an aldehyde of formula II with i) a cyanide source or nitromethane followed by ii) reduction with borane, lithium aluminum hydride or hydrogenation. Some compounds of formula II and III are also commercially available.

Compounds of formula (IV) may be prepared by reacting compounds of formula (III) with iii), acid chlorides in the presence of a suitable base such as triethylamine or 4-methylmorpholine. Typical reaction conditions comprise 1.0 equivalents of amine (III), 1.2-2.0 equivalents of base (preferably triethylamine), 1.1-1.3 equivalents of acid chloride in dichloromethane at 25° C.

Compounds of formula (V) may be prepared by reducing compounds of formula (IV) with iv), reducing agents such as borane or lithium aluminium hydride. Typical conditions 1.0 equivalents of amide (IV), 1.2-3.0 equivalents of borane in THF at reflux. Compounds of formula (V) ran also be made by reductive animation of compounds of formula (III) with a suitable aldehyde in the presence of sodium cyanoborohydride.

Compounds of formula (V) may be prepared by reacting compounds of formula V with v), chloroacetyl chloride or 2-substituted chloroacetyl chlorides (such as 2-chloropropionyl chloride or 2-chlorobutyryl chloride) in the presence of base such as triethylamine, sodium carbonate and potassium hydroxide. Typical conditions comprise 1.0 equivalents of amine IV, 1.0-1.3 equivalents of acid chloride, 1.2-2.0 equivalents of triethylamine in dichloromethane at 25° C., the crude reaction mixture is then dissolved in IPA with 1.2-3.0 equivalents of aqueous potassium hydroxide.

Compounds of formula (I) may be prepared by reacting compounds of formula (VI) with vi), reducing agents such as borane or lithium aluminium hydride. Typical conditions comprise 1.0 equivalents of amide VI, 1.2-3.0 equivalents of borane in THF at reflux.

The skilled man will appreciate that due to one of X, Y or Z being a hydroxy group, it will be necessary to protect the hydroxy group(s) with a suitable protecting group throughout the transformations of scheme 1, then remove the protecting group. Methods for deprotection of a phenol group depend on the protecting group. For examples of protection/deprotection methodology see "Protective groups in Organic synthesis", T W Greene and P G M Wutz. For example, where the hydroxy is protected as a methyl ether, deprotection conditions comprise refluxing in 48% aqueous HBr for 1-24 hours, or by stirring with borane tribromide in dichloromethane for 1-24 hours. Alternatively where the hydroxy is protected as a benzyl ether, deprotection conditions comprise hydrogenation with a palladium catalyst under a hydrogen atmosphere.

Compounds of general formula (I) where one of A or B is N, $R^1$ is H or $(C_1-C_6)$alkyl, $R^2$ is H and X, Y, and Z are as described herein, with the proviso that one of X, Y or Z is $NH_2$, may be prepared according to reaction scheme 2. Scheme is illustrated where B is C—Y and where Y is $NH_2$; the skilled man will understand that the alternative compounds are equally practicable.

Scheme 2

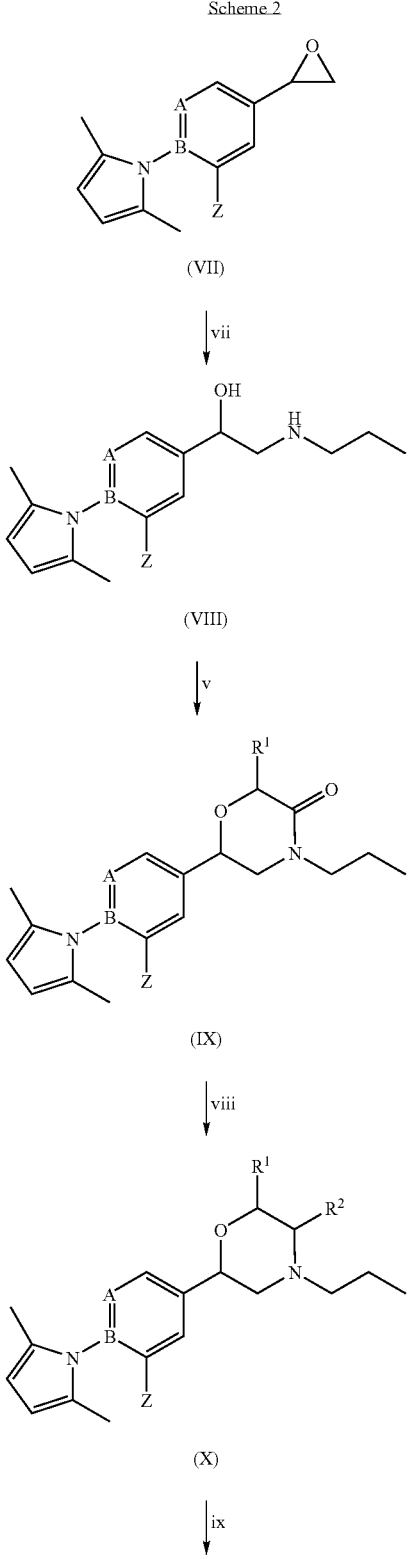

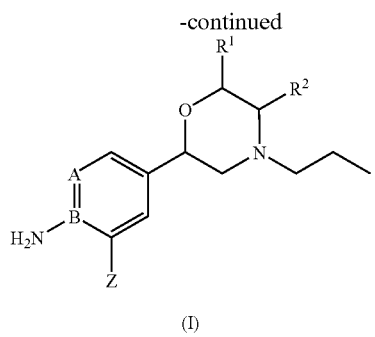

(I)

Compounds of formula (VII) may be prepared using the process as described in JP2001048864.

Compounds of formula (VII) may be prepared by reacting epoxide (VII) with vii), propylamine. Typical reaction conditions comprise stirring the epoxide with excess amine either neat or in dimethylsulphoxide.

Compounds of formula (IX) may be prepared by reacting compounds of formula (VIII) with v), chloroacetyl chloride or 2-substituted chloroacetyl chlorides (such as 2-chloropropionyl chloride or 2-chlorobutyryl chloride) in the presence of base such as triethylamine, sodium carbonate and potassium hydroxide. Typical conditions comprise 1.0 equivalents of amine (VIII), 1.2-2.0 equivalents of triethylamine in dichloromethane at 25° C., the crude reaction mixture is then dissolved in IPA with 1.2-3.0 equivalents of aqueous potassium hydroxide.

Compounds of formula (X) may be prepared by reacting compounds of formula (IX) with reducing agents such as lithium aluminium hydride. Typical conditions comprise 1.0 equivalents of amide (X), 1.2 equivalents of lithium aluminum hydride in THF at reflux.

Compounds of formula (I) may be prepared by ix), deprotection. Typical conditions comprise 1.0 equivalents of compound X and 5 equivalents of hydroxylamine hydrochloride in ethanol at reflux.

Compounds of general formula I, where A is C—X, B is C—Y, $R^1$ is H and $R^2$ is H or $(C_1-C_6)$alkyl and where X, Y and Z are as described herein may be prepared according to reaction scheme 3.

Scheme 3

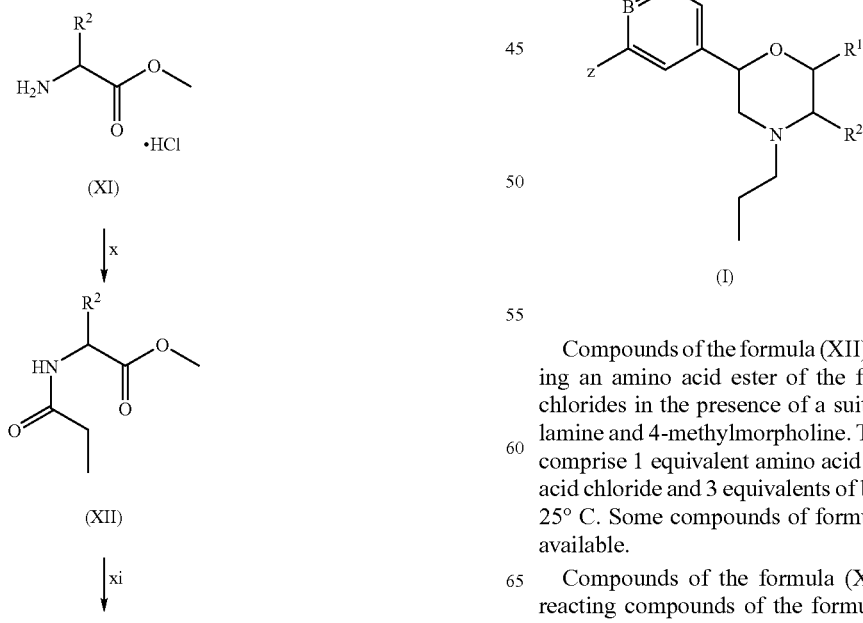

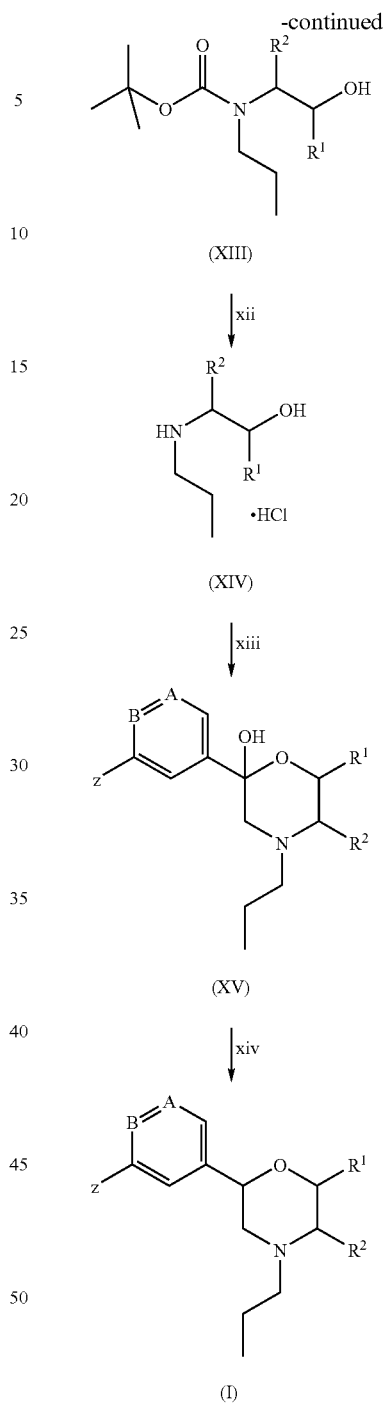

Compounds of the formula (XII) may be prepared by reacting an amino acid ester of the formula (XI) with x) acid chlorides in the presence of a suitable base such as triethylamine and 4-methylmorpholine. Typical reaction conditions comprise 1 equivalent amino acid ester (XI), 1 equivalent of acid chloride and 3 equivalents of base in dichloromethane at 25° C. Some compounds of formula (XI) are commercially available.

Compounds of the formula (XIII) may be prepared by reacting compounds of the formula (XII) with xi) borane-THF complex, with subsequent breaking of the boron-nitrogen complex with acid and t-butyloxycarbonyl protection of the formed amine. Typical reaction conditions comprise 1 equivalent of the amide (XII) with 3 equivalents of BH$_3$-THF in THF at reflux, cooling, cautious addition of 6M aqueous HCl, and heating to reflux for a further 6 h. Subsequent evaporation of solvent, redissolution in a methanol:water (8:1) mix, and addition of 5 equivalents of a base such as potassium hydroxide and 1.5 equivalents of di-tert-butyl dicarbonate, and stirring of the mixture for 72 hours.

Compounds of the formula (XIV) may be prepared by reacting compounds of the formula (XIII) with xii) an organic solution of HCl. Typical reaction conditions comprise 1 equivalent of the carbamate (XIII) and a 1-10 equivalents of a 4M solution of HCl in dioxan in dioxan at 25° C.

Compounds of the formula (XV) may be prepared by reacting compounds of the formula (XIV) with xiii) a 2-bromoacetophenone in the presence of a base such as triethylamine or 4-methylmorpholine. The 2-bromoacetophenones may be obtained from commercial sources or alternatively prepared from the parent acetophenone by standard bromination methodology well known to those skilled in the art. Typical conditions comprise 1 equivalent of the aminoalcohol (XIV) with 1-3 equivalents of triethylamine and 1 equivalent of a 2-bromoacetophenone at 65° C.

Compounds of the formula (I) may be prepared by reacting compounds of the formula (XV) with xiv) triethylsilane and trimethylsilyltriflate. Typical conditions comprise addition of 5-10 equivalents of triethylsilane to 1 equivalent of the morpholinol (XV) in dichloromethane at −78° C. followed by addition of 2 equivalents of trimethylsilyltriflate.

The skilled man will appreciate that due to one of X, Y or Z being a hydroxy group, it will be necessary to protect the hydroxy group(s) with a suitable protecting group throughout the transformations of scheme 3, then remove the protecting group. Methods for deprotection of a phenol group depend on the protecting group. For examples of protection/deprotection methodology see "Protective groups in Organic synthesis", T W Greene and P G M Wutz. For example, where the hydroxy is protected as a methyl ether, deprotection conditions comprise refluxing in 48% aqueous HBr for 1-24 hours, or by stirring with borane tribromide in dichloromethane for 1-24 hours. Alternatively where the hydroxy is protected as a benzyl ether, deprotection conditions comprise hydrogenation with a palladium catalyst under a hydrogen atmosphere.

Compounds of the formula (I) where the stereocentre alpha to the morpholine nitrogen is defined absolutely may be prepared starting from homochiral compounds of the formula (XI), which may be commercially available or obtained through methods readily available to the skilled man in the chemistry literature. The resulting compounds of the formula (I) will contain a mixture of diastereoisomers which may be separated on an HPLC column. Typical conditions comprise eluting through a Chiralcel OJ-H column with 100% MeOH mobile phase.

Compounds of general formula (I) where one of A or B is N, R$^1$ is H, R$^2$ is H or (C$_1$-C$_6$)alkyl and X, Y and Z are as described herein, with the proviso that one of X, Y or Z is NH$_2$, may be prepared according to reaction scheme 4. The scheme is illustrated where B is C—Y and where Y is NH$_2$; the skilled artisan will understand that the alternative compounds are equally practicable.

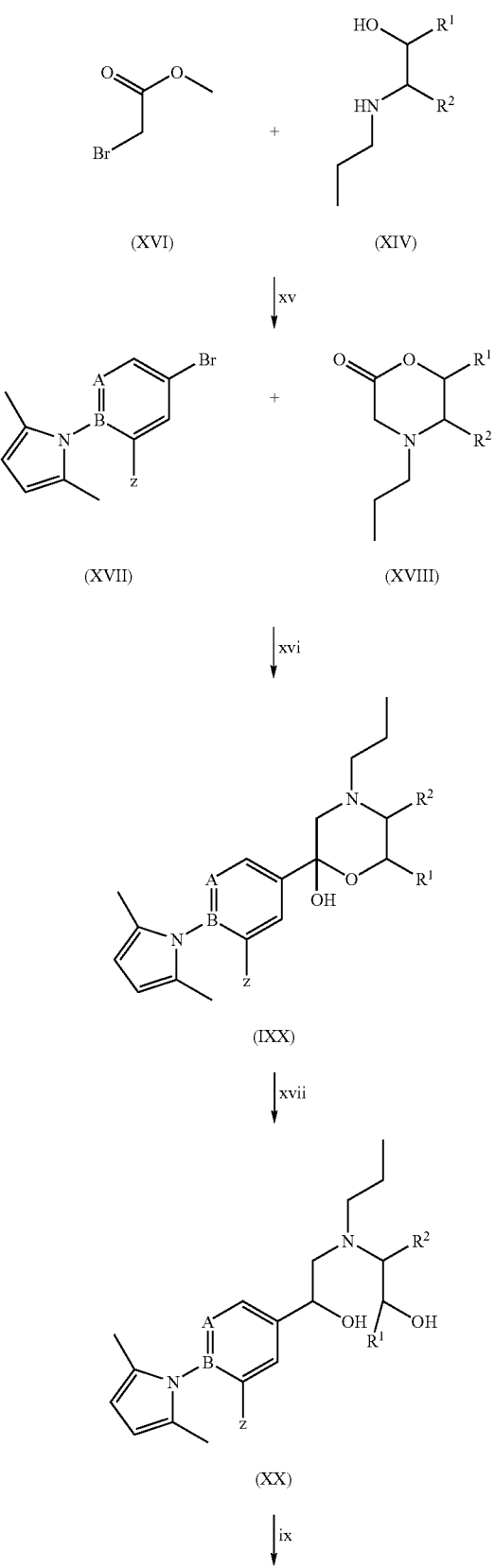

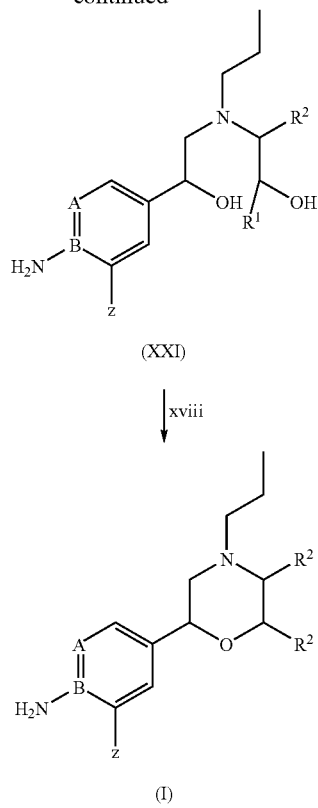

Compounds of formula (XVIII) may be prepared by reacting compounds of formula (XVI) with xv) amino alcohols of formula (XIV) in the presence of a base such as triethylamine or 4-methylmorpholine. Typical conditions comprise 1 equivalent of the aminoalcohol (XIV) with 1-3 equivalents of triethylamine and 1 equivalent of a compound of formula (XVI) using toluene as solvent at room temperature or above. Compounds of formula (XVI) are commercially available.

Compounds of formula (IXX) may be prepared by reacting a compound of formula (XVIII) with xvi) an organometallic reagent formed from the bromide of formula (XVII). Suitable organometallic reagents include Grignard (organomagnesium) or organolithium reagents, which may be prepared from the bromide by halogen metal exchange. Typical conditions comprise addition of isopropylmagensium chloride to the bromide (XVII) in an anhydrous ethereal solvent such as tetrahydrofuran at room temperature (to perform the halogen metal exchange reaction), followed by addition of the morpholinone (XVIII). The bromide (XVII) may be prepared using the process as described in WO9932475.

Morpholinol (IXX) may be reduced to diol (XX) by xvii) reaction with a hydride reducing agent, such as sodium borohydride in an alcohol solvent such as methanol.

Compounds of formula (XXI) may be prepared from the diol (XX) by ix), deprotection. Typical conditions comprise 1.0 equivalents of compound (XX) and 5 equivalents of hydroxylamine hydrochloride in ethanol at reflux.

Compounds of formula (I) may be prepared by xviii) cyclisation of compounds of formula (XXI) by treatment with acid. Typical conditions employ concentrated sulfuric acid and dichloromethane as solvent at room temperature or above.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto.

The compounds of the present invention have utility as selective D3 agonists in the treatment of disease states. There are a number of compounds with activity as both D2 and D3 agonists; however the use of such compounds is associated with a large number of side effects including nausea, emesis, syncope, hypotension and bradycardia, some of which are a cause for serious concern.

It was previously held that the efficacy of the prior art compounds stemmed from their ability to agonise D2; however D2 agonism is implicated as a cause of the side effects detailed above.

The present invention provides a class of selective D3 agonists. Serendipitously, these have been found to be efficacious, whilst reducing the side effects associated with unselective prior art compounds.

Compounds of present invention are useful in treating sexual dysfunction, female sexual dysfunction, including hypoactive sexual desire disorder, sexual arousal disorder, orgasmic disorder and sexual pain disorder; mate erectile dysfunction, hypertension, neurodegeneration, psychiatric disorders, depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

Compounds of the present invention are particularly suitable for treating female sexual dysfunction, male erectile dysfunction, neurodegeneration, depression and psychiatric disorders.

The compounds of the present invention are useful in male sexual dysfunction, particularly male erectile dysfunction. Male erectile dysfunction (MED), otherwise known as male erectile disorder, is defined as:

"the inability to achieve and/or maintain a penile erection for satisfactory sexual performance" (NIH Consensus Development Panel on Impotence, 1993)"

It has been estimated that the prevalence of erectile dysfunction (ED) of all degrees (minimal, moderate and complete impotence) is 52% in men 40 to 70 years old, with higher rates in those older than 70 (Melman et al 1999, J. Urology, 161, p 5-11). The condition has a significant negative impact on the quality of life of the individual and their partner, often resulting in increased anxiety and tension which leads to depression and low self-esteem. Whereas two decades ago, MED was primarily considered to be a psychological disorder (Benet et al 1994 Comp. Ther., 20: 669-673), it is now known that for the majority of individuals there is an underlying organic cause. As a result, much progress has been made in identifying the mechanism of normal penile erection and the pathophysiologies of MED.

Penile erection is a haemodynamic event which is dependent upon the balance of contraction and relaxation of the corpus cavemosal smooth muscle and vasculature of the penis (Lerner et al 1993, J. Urology, 149, 1256-1255). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure which results in an erection (Naylor, 1998, J. Urology, 81, 424-431).

The changes that occur during the erectile process are complex and require a high degree of co-ordinated control involving the peripheral and central nervous systems, and the endocrine system (Naylor, 1998, J. Urology, 81, 424-431). Corporal smooth muscle contraction is modulated by sympathetic noradrenergic innervation via activation of postsynaptic $\alpha_1$ adrenoceptors. MED may be associated with an increase in the endogenous smooth muscle tone of the corpus cavernosum. However, the process of corporal smooth muscle relaxation is mediated partly by non-adrenergic, non-cholinergic (NANC) neurotransmission. There are a number of other NANC neurotransmitters found in the penis, other than NO, such as calcitonin gene related peptide (CGRP) and vasoactive intestinal peptide (VIP). The main relaxing factor responsible for mediating this relaxation is nitric oxide (NO), which is synthesised from L-arginine by nitric oxide synthase (NOS) (Taub et al 1993 Urology, 42, 698-704). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ($[Ca^{2+}]_i$), via unknown mechanisms thought to involve protein kinase G activation (possibly due to activation of $Ca^{2+}$ pumps and $Ca^{2+}$-activated $K^+$ channels).

Multiple potential sites have been identified within the central nervous system for the modulation of sexual behaviour. The key neurotransmitters are thought to be serotonin, norepinephrine, oxytocin, nitric oxide and dopamine. By mimicking the actions of one of these key neurotransmitters sexual function may be adjusted. Dopamine D3 receptors are expressed almost exclusively in the limbic are of the brain, regions involved in the reward, emotional and cognitive processes.

Without being bound by any theory, it appears that "due to its role in the control of locomotor activity, the integrity of the nigrostriatal dopaminergic pathway is also essential for the display of copulatory behaviour. Somehow, more specific to sexual function, it is likely that dopamine can trigger penile erection by acting on oxytocinergic neurons located in the paraventricular nucleus of the hypothalamus, and perhaps on the pro-erectile sacral parasympathetic nucleus within the spinal cord". It now appears that the significant site is D3 and not as previously thought, D2.

In essence, D3 is an initiator of sexual behaviour.

Accordingly, the present invention provides for, the use of a compound of formula (I) in the preparation of a medicament for the treatment or prevention of erectile dysfunction.

Patients with mild to moderate MED should benefit from treatment with the compounds according to the present invention, and patients with severe MED may also respond. However, early investigations suggest that the responder rate of patients with mild, moderate and severe MED may be greater with a selective D3 agonist/PDE5 inhibitor combination. Mild, moderate and severe MED will be terms known to the man skilled in the art, but guidance can be found in The Journal of Urology, vol. 151, 54-61 (January 1994).

Early investigations suggest the below mentioned MED patient groups should benefit from treatment with a selective D3 agonist and a PDE5i (or other combination set out hereinafter). These patient groups, which are described in more detail in Clinical Andrology vol. 23, no. 4, p 773-782 and chapter 3 of the book by I. Eardley and K. Sethia "Erectile Dysfunction-Current Investigation and Management, published by Mosby-Wolfe, are as follows: psychogenic, organic, vascular, endocrinologic, neurogenic, arteriogenic, drug-induced sexual dysfunction (lactogenic) and sexual dysfunction related to cavernosal factors, particularly venogenic causes. Accordingly the present invention provides for the use of a compound of formula (I), (Ia) or (Ib) in the preparation of a medicament in combination with a PDE5 inhibitor for the treatment of erectile dysfunction.

Suitable PDE5 inhibitors are described herein.

The compounds of the present invention are useful in the treatment or prevention of female sexual dysfunction (FSD), particularly FSAD.

In accordance with the invention, FSD can be defined as the difficulty or inability of a woman to find satisfaction in sexual expression. FSD is a collective term for several diverse female sexual disorders (Leiblum, S. R. (1998)—Definition and classification of female sexual disorders. *Int. J. Impotence Res.,* 10, S104-S106; Berman, J. R., Berman, L. & Goldstein, I. (1999)—Female sexual dysfunction: Incidence, pathophysiology, evaluations and treatment options. *Urology,* 54, 385-391.). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998)—Definition and classification of female sexual disorders. *Int. J. Impotence Res.,* 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin re-uptake inhibitors (SSRIs) or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

As previously discussed, D3 is thought to be an initiator of sexual behaviour. The clitoris is considered to be a homologue of the penis (Levin, R. J. (1991), Exp. Clin. Endocrinol., 98, 61-69); the same mechanism that provides provides an erectile response in the male produces an increase in genital blood flow in the female with an associated effect upon FSD. In addition there are changes in proceptivity and receptivity.

Thus, in accordance with a preferred aspect of the invention, there is provided use of a compound of formula (I), (Ia) or (Ib) in the preparation of a medicament for the treatment or prophylaxis of female sexual dysfunction, more particularly hypoactive sexual desire disorder, sexual arousal disorder, orgasmic disorder and sexual pain disorder.

Preferably the compounds of formula (I) are useful in the treatment or prophylaxis of sexual arousal disorder, orgasmic disorder, and hypoactive sexual desire disorder, and most preferably in the treatment or prophylaxis of sexual arousal disorder.

In a preferred embodiment the compounds of formula (I), (Ia) and (Ib) are useful in the treatment of a subject with female sexual arousal disorder and concomitant hypoactive sexual desire disorder.

The Diagnostic and Statistical Manual (DSM) IV of the American Psychiatric Association defines Female Sexual Arousal Disorder (FSAD) as being:

"... a persistent or recurrent inability to attain or to maintain until completion of the sexual activity adequate lubrication-swelling response of sexual excitement. The disturbance must cause marked distress or interpersonal difficulty. . . . ".

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post-menopausal (±hormone replacement therapy (HRT)) women. It is associated with concomitant disorders such as depression, cardiovascular diseases, diabetes and urogenital (UG) disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., Int. J. Impot. Res., 10, S84-S90, 1998) with animal data supporting this view (Park et al., Int. J. Impot. Res., 9, 27-37, 1997).

R. J. Levin teaches us that because "... male and female genitalia develop embryologically from the common tissue anlagen, [that] male and female genital structures are argued to be homologues of one another. Thus the clitoris is the penile homologue and the labia homologues of the scrotal sac. . . . " (Levin, R. J. (1991), Exp. Clin. Endocrinol., 98, 61-69).

Drug candidates for treating FSAD, which are under investigation for efficacy, are primarily erectile dysfunction therapies that promote circulation to male genitalia.

The compounds of the present invention are advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response.

Thus, in accordance with a preferred aspect of the invention, there is provided use of a compound of formula (I), (Ia) or (Ib) in the preparation of a medicament for the treatment or prophylaxis of female sexual arousal disorder.

By female genitalia herein we mean: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C. D. Clemente, 13th American Edition).

The compounds of the invention find application in the following sub-populations of patients with FSD: the young, the elderly, pre-menopausal, peri-menopausal, post-menopausal women with or without hormone replacement therapy.

The compounds of the invention find application in patients with FSD arising from:
i) Vasculogenic etiologies e.g. cardiovascular or atherosclerotic diseases, hypercholesterolemia, cigarette smoking, diabetes, hypertension, radiation and perineal trauma, traumatic injury to the iliohypogastric pudendal vascular system.
ii) Neurogenic etiologies such as spinal cord injuries or diseases of the central nervous system including multiple sclerosis, diabetes, Parkinsonism, cerebrovascular accidents, peripheral neuropathies, trauma or radical pelvic surgery.
iii) Hormonal/endocrine etiologies such as dysfunction of the hypothalamic/pituitary/gonadal axis, or dysfunction of the ovaries, dysfunction of the pancreas, surgical or medical castration, androgen deficiency, high circulating levels of prolactin e.g. hyperprolactinemia, natural menopause, premature ovarian failure, hyper and hypothyroidism.

iv) Psychogenic etiologies such as depression, obsessive compulsive disorder, anxiety disorder, postnatal depression/"Baby Blues", emotional and relational issues, performance anxiety, marital discord, dysfunctional attitudes, sexual phobias, religious inhibition or a traumatic past experiences.

v) Drug-induced sexual dysfunction resulting from therapy with selective serotonin reuptake inhibitors (SSRis) and other antidepressant therapies (tricyclics and major tranquillizers), anti-hypertensive therapies, sympatholytic drugs, chronic oral contraceptive pill therapy.

The Compounds of the present invention are also useful in the treatment of depression.

Dopamine D3 receptors are expressed almost exclusively in the limbic area of the brain, regions involved in reward, emotional and cognitive processes. Chronic treatment with several classes of antidepressants are known to increase the expression of D3 in the limbic area, and antidepressant effects of desipramine can be blocked by sulpride (D2/D3 antagonist) when injected to nucleus accumbens (area rich in D3) but not caudate-putamen (area rich in dopamine D2 receptors). In addition, antidepressant effects were observed preclinical models of depression and in patients treated with pramipexole, a D3-preferring agonist. The available information suggests that D3 receptors mediate the anti-depressant activity and that selective D3 receptor agonists represent a new class of antidepressant drugs. Since antidepressants are known to be effective in other psychiatric disorders, D3 agonists would have the potential to treat psychiatric diseases.

The present invention provides for the use of a selective D3 agonist in the preparation of a medicament for the treatment of depression and psychiatric diseases.

Preferably said D3 agonist exhibit a functional potency at D3 receptor expressed as an EC50, lower than 1000 nM, more preferably lower than 100 nM, yet more preferably lower than 50 nM, most preferably lower than 10 nM.

Preferably said D3 agonist has a selectivity for D3 over D2, wherein said dopamine D3 receptor agonist is at least about 15-times, preferably at least about 27-times, more preferably at least about 30-times, most preferably at least about 100-times more functionally selective for a dopamine D3 receptor as compared with a dopamine D2 receptor Suitable conditions include depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, eating disorders (e.g. anorexia nervosa and bulimia nervosa), obesity, chemical dependencies (e.g. addictions to alcohol, cocaine, heroin, phenobarbital, nicotine and benzodiazepines), Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, negative symptoms of schizophrenia, stress incontinence, Tourette's syndrome, trichotillomania, kleptomania, attention deficit hyperactivity disorder (ADHD), chronic paroxysmal hemicrania, emotional lability, pathological crying, sleeping disorder (cataplexy) and shock.

In a preferred embodiment, the present invention provides for the use of a compound of formula (I), (Ia) and (Ib) in the preparation of a medicament for the treatment of depression or psychiatric disorders.

Suitable depressive conditions and psychiatric disorders are described above.

The compounds of the present invention also have utility in the treatment of neurodegeneration; sources of neurodegeneration include neurotoxin poisoning, vision loss caused by neurodegeneration of the visual pathway, such as by a stroke in the visual pathway eg in retina, optic nerve and/or occipital lobe; epileptic seizures; and from impairment of glucose and/or oxygen supply to the brain.

Accordingly the present invention provides for the use of a selective D3 agonist in the preparation of a medicament for the treatment of neurodegeneration.

Preferably said D3 agonist exhibit a functional potency at D3 receptor expressed as an EC50, tower than 1000 nM, more preferably lower than 100 nM, yet more preferably lower than 50 nM, most preferably lower than 10 nM.

Preferably said D3 agonist has a selectivity for D3 over D2, wherein said dopamine D3 receptor agonist is at least about 15-times, preferably at least about 27-times, more preferably at least about 30-times, most preferably at least about 100-times more functionally selective for a dopamine D3 receptor as compared with a dopamine D2 receptor In a preferred embodiment, the D3 agonist is a compound of formula (I), (Ia) or (Ib)

In addition to their role in treating Sexual dysfunction, depression, neurodegeneration and psychiatric disorders, the compounds of the present invention are likely to be efficacious in a number of additional indications.

Accordingly, the present invention provides for the use of compounds of formula (I), (Ia) or (Ib) in the preparation of a medicament for the treatment of hypertension, premature ejaculation, obesity, cluster headache, migraine, pain, endocrine disorders (e.g. hyperprolactinaemia), vasospasm (particularly in the cerebral vasculature), cerebellar ataxia, gastrointestinal tract disorders (involving changes in motility and secretion), premenstrual syndrome, fibromyalgia syndrome, stress incontinence, trichotillomania and chronic paroxysmal hemicrania, headache (associated with vascular disorders).

D3/D2 AGONIST BIND ASSAY

Gonazalez et at (Eup. J Pharmacology 272 (1995) R1-R3) discloses an assay for determining the binding capability of a compound at D3 and/or D2 dopamine receptors and thus the binding selectivity of such compounds. This assay is, thus, herein referred to as a binding assay.

D3/D2 AGONIST FUNCTIONAL ASSAY

A suitable assay for determining functionally the activity of a compound at D3 and/or D2 dopamine receptors is detailed hereinbelow.

Compounds are evaluated as agonists or antagonists at the dopamine D2 and D3 receptors by looking at cAMP levels in a GH4C1 and CHO cell-line expressing the human D2 and D3 receptors, respectively.

Experimental Procedures

Inhibition Via Dopamine D3 Receptors of Forskolin-Stimulated Adenylate Cyclase Activity

Materials

Cell Culture Media:

| hD$_3$CHO Medium |
| --- |
| DMEM, high glucose (Sigma D5671) |
| 2 mM L-Glutamine (Sigma G7513) |
| 10% dialyzed FBS (Sigma F0392) | hD$_3$CHO (Chinese hamster Ovary) cells expressing the human Dopamine D3 receptor were generated in house. These cells are deficient in the dihydrofolate reductase gene. Media is made up fresh every week as below, and filtered through a 0.22 µM filter before use. Media is stored at 4° C. and warmed to 37° C. prior to addition to the cells.

Cell Dissociation Solution (CDS): (Sigma C-5914)
    5 ml used to harvest cells from 225 cm$^2$ flask (37° C. 5 min for hD2LGH4C1 cells and 10 minutes for hD3CHO cells).

Phosphate Buffered Saline (PBS): (Gibco. 14040-091)

Trypan Blue: (Sigma T8154)

Forskolin (Calbiochem 344273)
    Dissolved to a concentration of 20 mM in distilled water, (This stock is stored at +4° C.). 4× assay stock of 40 µM is made by carrying out a 500-fold dilution in PBS buffer. 25 µl of the 40 µM stock is added to a final assay volume of 100 µl, yielding a final assay concentration of 10 µM.

Test Compounds
    Dissolved in 100% DMSO to yield a stock concentration of 10 mM.

Pramipexole Standard
    Dissolved in 100% DMSO to yield a stock concentration of 10 mM.

Cyclase Activation Flashplate Assay (NEN SMP004B)
    Supplied by Perkin-Elmer Life Sciences Inc

[$^{125}$I]-cyclic Adenosine Monophosphate (cAMP) (NEX 130)
    Supplied by Perkin-Elmer Life Sciences, Inc Specific Equipment
    Westbait Microtitre Plate Shaker/Incubator
    Packard Topcount NXT (ECADA compatible programme)
    Tecan Genesis
    Labsystems Multi-drop DW

Protocol Testing Compound Activity with hD$_3$CHO Cells

Compound Dilutions
    Pramipexole is included as a reference standard. A 10-point, semi-log curve is generated every 4 plates. Compound results are normalised to the minimum (0 nM pramipexole) and maximum (100 nM pramipexole) responses generated by the cells. All test compounds may also be tested via a 10-point (semi-log) curve.
    Test compounds are dissolved in 100% DMSO to yield a stock concentration of 10 mM. These are further diluted in 100% DMSO to 1 mM via a 10-fold dilution (1000× the final assay concentration required, e.g. 1 mM will give a top concentration of 1 µM).
    Pramipexole is dissolved in 100% DMSO to give a concentration of 10 mM. Pramipexole is diluted further to 0.1 mM in 100% DMSO via a 100-fold dilution.
    Further dilutions and additions are carried out in 0.4% DMSO/PBS using a suitable Tecan Genesis Protocol, capable of performing serial dilutions at a fold of 3.159 (semi-log unit).

Tecan Genesis Dilutions

10 µL of the test compounds are added to column 1 of a microplate. 240 µL of 0.4% DMSO/PBS is added to this to give a 25-fold dilution (0.04 mM). 20 µL of the 0.04 mM dilution is transferred to the wells of column 2 where 180 µL of 0.4% DMSO/PBS is added, giving a further 10-fold dilution to achieve a 4× top assay concentration (0.004 mM).

Serial dilutions are performed (3.159-fold) to achieve a semi-log dilution series:
    4 µM, 1.27 µM, 400 nM, 127 nM, 40 nM, 13 nM, 4 nM, 1.27 nM, 0.4 nM, 0.1 nM 25 µL (in duplicate) of the serial dilutions are transferred to columns 2-11 of the Flashplate (See Appendix). Since the final assay volume is 100 µL the final assay concentrations will be:
    1000 µM, 317 nM, 100 nM, 32 nM, 10 nM, 3.2 nM, 1 nM, 0.3 nM, 0.1 nM 0.03 nM Minimum control (low control): 25 µL 0.4% DMSO/PBS (vehicle) is added to the following wells (column 1 wells E-H and column 2 wells A-D). Cells+forskolin are added later.

Maximum control (high control): 10 mM pramipexole is diluted in PBS via a 250-fold dilution (10 µL+2490 µL PBS) to generate 40 µM pramipexole. 40 µM pramipexole is further diluted via a 100-fold dilution in 0.4% DMSO/PBS (100 µL+9900 µL Vehicle) to generate 400 nM (4× assay concentration of the standard pramipexole). 25 µL of 400 nM pramipexole is added to the following welts of the Flashplate to yield 100 nM pramipexole final, column 1 wells A-D and column 12 wells E-H. Cells+forskolin are added later.

Cyclase-activation Flashplate Assay. (NEN SMP004B)
    As described in the Materials section, forskolin is dissolved in distilled water to achieve a stock concentration of 20 mM. This is further diluted to 40 µM (4× assay concentration) using PBS. 25 µL of 40 µM stock is added to all wells using a Multi-drop, giving a final concentration of 10 µM. Plates are then sealed and incubated at 37.0 in a Westbart incubator while cells are harvested.
    Cells are harvested from flasks, which are between 70%-80% confluent. It is essential that all components added to the cells are warned to 37° C. 5 mL of CDS is added per T225 flask and incubated at 37° C. for 5 minutes before being neutralised with 5 mL PBS. The cells are then centrifuged at 160 g (1000 rpm) for 5 minutes. The resultant supernatant is discarded and cells are re-suspended in Stimulation Buffer (warmed to 37° C.), to achieve 5×10$^5$ cells/ml. 50 µl of cell suspension is then dispensed into all wells of the Flashplate.
    Plates are immediately incubated at 37° C. on a shaking incubator for 15 minutes. The reaction is terminated with 100 µl of Detection Mix in all wells (100 µL $^{125}$I cAMP; 11 ml Detection buffer per plate).

Plates are re-sealed and incubated in the dark for 3 hours to allow equilibrium between the anti-cAMP antibody (coating the wells), [$^{125}$I]-cAMP tracer and cellular cAMP.

Plates are counted on a Packard Topcount NXT using a suitable ECADA compatible protocol (Protocol 75)

Resuscitation Of Frozen Ampoules

Remove ampoules from liquid nitrogen and allow them to equilibrate for 2 minutes as trapped gas or liquid may cause the ampoule to expand rapidly and explode. They can also be placed at minus 20° C. for 2 minutes before thawing.

Thaw ampoules quickly and completely at 37° C. in a water bath.

Transfer cell suspension to a 75 cm$^2$ flask containing 10 mL growth media and incubate for 24 h at 37° C. 5% CO$_2$. After cell attachment (3-6 hours) media is removed and replaced with fresh media (to remove DMSO). After 24 h, if approaching confluency, cells are transferred to a 225 cm$^2$ flask. If not, the cells are maintained until they are 70%-80% confluent.

Cell Harvesting and Splitting

Cells are split on a Friday to provide cells for assays on Monday and Tuesday. Cells required for the remainder of the week are split on a Monday.

It is essential not to allow the hD$_3$CHO cells grow beyond 80% confluence, or to create splits >1:20, as this has detrimental effects on their proliferative response and will subsequently effect the cells ability to perform in the assay.

Cells are grown in 225 cm$^2$ flasks (Jumbos). Every component added to the cents must be warmed to 37° C. before use.

Cell Harvest

Growth media is removed from flasks and cells are washed with warm PBS (Gibco. 14040-091) and removed.

5 mL of cell dissociation buffer is added to cells and placed in incubator for approx. 5 minutes.

Flasks given a sharp tap to dislodge any remaining cells from the tissue culture plastic.

5 mL of PBS is added to the cells and used to wash the base and of the flask. Cells are centrifuged for 5 minutes at 160 g (1000 rpm) to pellet the cells.

Supernatant is discarded and 5 mL of Stimulation Buffer is used to re-suspend the cells. A trypan blue exclusion assay is carried out to determine the number of viable cells.

Cells are diluted in Stimulation Buffer to yield a concentration of 5×10$^5$ cells/ml.

To passage to cells the centrifugation step is omitted and the cell suspension is dispensed into new T225 flasks containing 50 mL media.

Split Ratios hD$_3$CHO are split between 1:5 to 1:10. The culture cannot be continued beyond passage 30 as cell line characteristics are lost with increased passage.

Cryopreservation of Cell Lines

It is essential to create a cell bank of your own cells to resuscitate for further use.

Cells are harvested as described in the previous section. Following the trypan blue exclusion assay, cells are diluted in medium containing 10% DMSO to achieve 2 to 4×10$^6$ cells/ml.

Cells are divided into 1 ml aliquots and immediately frozen down gradually, in a 'Mr Frosty', (containing fresh IPA) at −80° C. prior to being transferred to a gaseous-phase liquid-nitrogen storage vessel, (Cells may be stored in the 'Mr Frosty' for up to 2 days).

It is advisable to test the cell viability by thawing one ampoule after freezing. Viabilities below 70% may cause problems on recovery due to low cell numbers and the presence of debris.

Data Analysis

The data is analysed using ECADA.

% Normalisation (in relation to pramipexole) is generated for all compounds via the following formulae:

$$\% \text{ Normalisation} = (X-B0)/(\text{Max}-B0) \times 100$$

where, x=Average net counts for a given concentration of test compound,

Bo=Average net counts of minimum control (0 nM of Pramipexole) and,

Max=Average net counts given of maximum control (100 nM Pramipexole)

Curves can be generated by plotting % normalisation (y) versus concentration of agonist in nM (x). Data is fitted using non-linear regression with the slope constrained to 1. From this, an EC50 and % Emax for the test compound are determined.

Assay Plate Layout (10-point EC50):

|   | 1 | 2 | 3 | 4 | 5 | 6 | 7 | 8 | 9 | 10 | 11 | 12 |
|---|---|---|---|---|---|---|---|---|---|----|----|----|
| A | MAX | C1 |  |  |  |  |  |  |  |    |    | MIN |
| B | MAX | C1 |  |  |  |  |  |  |  |    |    | MIN |
| C | MAX | C2 |  |  |  |  |  |  |  |    |    | MIN |
| D | MAX | C2 |  |  |  |  |  |  |  |    |    | MIN |
| E | MIN | C3 |  |  |  |  |  |  |  |    |    | MAX |
| F | MIN | C3 |  |  |  |  |  |  |  |    |    | MAX |
| G | MIN | C4 |  |  |  |  |  |  |  |    |    | MAX |
| H | MIN | C4 |  |  |  |  |  |  |  |    |    | MAX |

Column 1: Wells A-D = MAX: High Controls (cells + forskolin + 100 nM pramipexole)
Wells E-H = MIN: Low Controls (cells + forskolin + vehicle)
Column 12: Wells A-D = MIN: Low Controls (cells + forskolin + vehicle)
Wells E-H = MAX: High Controls (cells + forskolin + 100 nM pramipexole)
Columns 2-11: 10-point serial dilutions (in duplicate) of test-compounds.
Decreasing concentrations from columns 2 to 11 (1000 nM to 0.03 nM).
Pramipexole replaces C1 in first plate.

Inhibition Via Dopamine D2 Receptors of Forskolin Stimulated Adenylate Cyclase Activity Materials Cell Culture Media:

| HD2 GH4C1/hD$_{2L}$ Medium |
|---|
| Hams F-12 (Sigma N6013) |
| 2 mM L-Glutamine (Sigma G7513) |
| 10% FBS (Gibco 10106-169) |
| 700 µg/ml Geneticin (Gibco 10131-019) |

GH4C1/hD$_{2L}$ are rat pituitary cells expressing the human dopamine D2$_{long}$ receptor.

Media is made up fresh every week as below and filtered through a 0.22 µM filter before use. Media is stored at 4° C. and warmed to 37° C. for addition to the cells.

Cell Dissociation Solution (CDS): (Sigma C-5914)
  5 mL used to harvest cells from 225 cm² flask Phosphate Buffered Saline (PBS): (Gibco. 14040-091)

Trypan Blue: (Sigma T8154)

Forskolin (Calbiochem 344273)
  Dissolved to a concentration of 20 mM in distilled water. (This stock is stored at +4° C.).
  4× assay stock of 20 µM made by carrying out a 1000-fold dilution in PBS buffer. 25 µl of the 20 µM stock is added to a final assay volume of 100 µl, giving a final assay concentration of 5 µM.

Test Compounds
  Dissolved to a concentration of 10 mM in 100% DMSO

Pramipexole Standard
  Dissolved in 100% DMSO to yield a final stock concentration of 10 mM.

Cyclase Activation Flashplate Assay (NEN SMP004B)
  Supplied by Perkin-Elmer Life Sciences. Inc

[$^{125}$I]-Cyclic Adenosine Monophosphate (cAMP) (NEX 130)
  Supplied by Perkin-Elmer Life Sciences, Inc Specific Equipment
Westbart Microtitre Plate Shaker/Incubator
Packard Topcount NXT (ECADA compatible programme)
Tecan Genesis
Labsystems Multi-drop DW Protocols Compound Dilutions
  Pramipexole is included as a reference standard A 10-point, semi-log curve is generated every 4 plates. Compound responses are normalised to the minimum (0 nM pramipexole) and maximum (1000 nM Pramipexole) responses generated by the cells. All test compounds may also be tested via a 10-point (semi-log) curve.
  Test compounds are dissolved in 100% DMSO to yield a stock concentration of 10 mM, (1000× the final assay concentration required, e.g. 10 mM will give a top concentration of 10000 nM).
  Pramipexole is dissolved in 100% DMSO to give a concentration of 10 mM. Pramipexole is diluted further to 1 mM in 100% DMSO via a 10-fold dilution.
  Further dilutions and additions are carried out in 0.4% DMSO/PBS using a suitable Tecan Genesis Protocol which is capable of performing serial dilutions at a fold of 3.159 (semi-bog unit).

Tecan Genesis Dilutions

10 µL of the test compounds are added to column 1 of a microplate, 240 µL of 0.4% DMSO/PBS is added to this to give a 25-fold dilution (0.4 mM). 20 µL of the 0.4 mM dilution is transferred to wells of column 2 where 180 uL of 0.4% DMSO/PBS is added, giving a further 10-fold dilution to achieve a 4× top assay concentration (0.04 mM).
  Serial dilutions are performed (3.159-fold) to achieve a semi-log dilution series.
    40 µM, 12.7 µl M, 4 µM, 1.27 µM, 400 nM, 130 nM, 40 nM, 13 nM, 4 nM, 1.3 nM 25 µL (in duplicate) of the serial dilutions are transferred to columns 2-11 of the Flashplate (See Appendix). Since the finals assay volume is 100 µL, the final assay concentrations will be:
    10,000 uM, 3170 nM, 1000 nM, 320 nM, 100 nM, 32 nM, 10 nM, 3 nM, 1 nM, 0.3 nM
  Minimum control (low control): 25 µL of 0.4% DMSO/PBS (vehicle) is added to the following wells (column 1 wells E-H and column 2 wells A-D). Cells and forskolin are added later.
  Maximum control (high control): 10 mM pramipexole is diluted in PBS via a 250-fold dilution (10 µL+2490 µL PBS) to generate 40 µM pramipexole. 40 µM pramipexole is further diluted via a 10-fold dilution in 0.4% DMSO/PBS (100 µL+990 µL Vehicle) to generate 4000 nM (4× assay concentration of the standard pramipexole). 25 µL of 4000 nM pramipexole is added to the following wells of the Flashplate to yield 1000 nM pramipexole final; column 1 wells A-D and column 12 wells E-H. Cells+forskolin are added later.

Cyclase-activation Flashplate Assay, (NEN SMP004B)
  As described in the Materials section, forskolin is dissolved in distilled water to achieve a stock concentration of 20 mM. This is further diluted to 20 µM (4× assay concentration) using PBS. 25 µL is added to all wells using a Multi-drop, giving a final concentration of 5 µM. Plates are then sealed and incubated at 37° C. in a Westbart incubator while cells are harvested.
  Cells are harvested from flasks which are between 70%-80% confluent. It is essential that all components added to the cells are warmed to 37° C. 5 mL of CDS is added per 225 cm² flask, and incubated at 37° C. for 5 minutes before being neutralised with 5 mL PBS. The cells are then centrifuged at 160 g (1000 rpm) for 5 minutes. The resultant supernatant is discarded and cells are re-suspended in Stimulation Buffer (warmed to 37° C.), to achieve 1×10$^5$ cells/ml. 50 µl of cell suspension is then dispensed into all wells of the Flashplate.
  Plates are immediately incubated at 37° C. on a shaking incubator for 15 minutes. The reaction is terminated with 100 µl of Detection Mix in all wells (100 µL $^{125}$I cAMP: 11 ml Detection buffer plate).
  Plates are re-sealed and incubated in the dark for 3 hours to allow equilibrium between the anti-cAMP antibody (coating the wells), [$^{125}$I]-cAMP tracer and cellular cAMP.
  Plates are counted on a Packard Topcount NXT using a suitable ECADA compatible protocol (Protocol 75)

Resuscitation of Frozen Ampoules

Remove ampoules from liquid nitrogen and allow them to equilibrate for 2 minutes as trapped gas or liquid may cause the ampoule to expand rapidly and explode. They can also be placed at minus 20° C. for 2 minutes before thawing.
  Thaw ampoules quickly and completely at 37° C. in a water bath.
  Transfer cell suspension to a 75 cm² flask containing 10 mL growth media and incubate for 24 h at 37° C., 5% $CO_2$. After cell attachment (3-6 hours) media is removed and replaced with fresh media (to remove DMSO). After 24 h, if approaching confluency, cells are transferred to a 225 cm² flask. If not, the cells are maintained until they are 60% confluent.

Cell Harvesting and Splitting

Cells are split on a Friday to provide cells for assays on Monday and Tuesday. Cells required for the remainder of the week are split on a Monday.

It is essential not to allow the cells grow beyond 60% confluence as this has detrimental effects on their proliferative response and will subsequently effect the cells ability to perform in the assay.

Cells are grown in 225 cm$^2$ flasks (Jumbos). Every component added to the cells must be warmed to 37° C. before use.

Cell Harvest

Growth media is removed from flasks and cells are washed with warm PBS (Gibco. 14040-091) and removed.
- 5 mL of cell dissociation buffer is added to cells and placed in incubator for approx. 5 minutes.
- Flasks given a sharp tap to dislodge any remaining cells from the tissue culture plastic.
- 5 mL of PBS is added to the cells and used to wash the base and of the flask. Cells are centrifuged for 5 minutes at 160 g (1000 rpm) to pellet the cells.
- Supernatant is discarded and 5 mL of Stimulation Buffer is used to re-suspend the cells. A trypan blue exclusion assay is carried out to determine the number of viable cells.
- Cells are diluted in Stimulation Buffer to yield a concentration of 1×10$^5$ cells/ml.
- To passage to cells the centrifugation step is omitted and the cell suspension is dispensed into new T225 flasks containing 50 mL media.

Split Ratios

GH4C1/D2 are split between 1:3 to 1:5.

Cryopreservation of Cell Lines

It is essential to create a cell bank of your own cells to resuscitate for further use.
- Cells are harvested as described in the previous section. Following the trypan blue exclusion assay, cells are diluted in medium containing 10% DMSO to achieve 2 to 4×10$^6$ cells/ml.
- Cells are divided into 1 ml aliquots and immediately frozen down gradually, in a 'Mr Frosty', (containing fresh IPA) at −80° C. prior to being transferred to a gaseous-phase liquid-nitrogen storage vessel, (Cells may be stored in the 'Mr Frosty' for up to 2 days).

It is advisable to test the cell viability by thawing one ampoule after freezing. Viabilities below 70% may cause problems on recovery due to low cell numbers and the presence of debris.

Data Analysis

The data is analysed using ECADA.

% Normalisation (in relation to pramipexole) is generated for all compounds via the following formulae:

% Normalisation = $(X-B0)/(Max-B0) \times 100$ where, x=Average net counts for a given concentration of test compound, Bo=Average net counts of minimum control (0 nM of Pramipexole) and, Max=Average net counts given of maximum control (100 nM Pramipexole)

Curves can be generated by plotting % normalisation (y) versus concentration of agonist in nM (x). Data is fitted using non-linear regression with the slope constrained to 1. From this, an EC50 and % Emax for the test compound are determined.

Assay Plate Layout (10-point EC50):

|   | 1 | 2 | 3 | 4 | 5 | 6 | 7 | 8 | 9 | 10 | 11 | 12 |
|---|---|---|---|---|---|---|---|---|---|----|----|----|
| A | MAX | C1 |   |   |   |   |   |   |   |    |    | MIN |
| B | MAX | C1 |   |   |   |   |   |   |   |    |    | MIN |
| C | MAX | C2 |   |   |   |   |   |   |   |    |    | MIN |
| D | MAX | C2 |   |   |   |   |   |   |   |    |    | MIN |
| E | MIN | C3 |   |   |   |   |   |   |   |    |    | MAX |
| F | MIN | C3 |   |   |   |   |   |   |   |    |    | MAX |
| G | MIN | C4 |   |   |   |   |   |   |   |    |    | MAX |
| H | MIN | C4 |   |   |   |   |   |   |   |    |    | MAX |

Column 1: Wells A-D = MAX: High Controls (cells + forskolin + 100 nM pramipexole)
Wells E-H = MIN: Low Controls (cells + forskolin + vehicle)
Column 12: Wells A-D = MIN: Low Controls (cells + forskolin + vehicle)
Wells E-H = MAX: High Controls (cells + forskolin + 100 nM pramipexole)
Columns 2-11: 10-point serial dilutions (in duplicate) of test-compounds. Decreasing concentrations from columns 2 to 11 (1000 nM to 0.03 nM). Pramipexole replaces C1 in first plate.

Using the assay described above, the compounds of the present invention all exhibit a functional potency at D3 receptor expressed as an EC50, lower than 1000 nM and a 10 fold selectivity for D3 over D2.

Compound of example 8 has a functional potency at D3 receptor expressed as an EC50: of 7.6 nM and 1315.8 fold selectivity for D3 over D2. Selectivity is calculated as the D2 EC50 value divided by the D3 EC50 value. Where the value of the D2 EC50 was >10000, a figure of 10000 was used in the calculation.

It is to be appreciated that all references herein to treatment include curative, palliative and prophylactic treatment.

Suitable auxiliary active agents for use in the combinations of the present invention include:

1) Naturally occurring or synthetic prostaglandins or esters thereof. Suitable prostaglandins for use herein include compounds such as alprostadil, prostaglandin $E_1$, prostaglandin $E_0$, 13,14-dihydroprosta glandin $E_1$, prostaglandin $E_2$, eprostinol, natural synthetic and semi-synthetic prostaglandins and derivatives thereof including those described in WO-00033825 and/or U.S. Pat. No. 6,037,346 issued on 14 Mar. 2000 all incorporated herein by reference, $PGE_0$, $PGE_1$, $PGA_1$, $PGB_1$, $PGF_1\alpha$, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3\alpha$, carboprost tromethamine dinoprost, tromethamine, dinoprostone, lipo prost, gemeprost, metenoprost, sulprostune, tiaprost and moxisylate;

2) α-adrenergic receptor antagonist compounds also known as α-adrenoceptors or α-receptors or α-blockers. Suitable compounds for use herein include; the α-adrenergic receptor blockers as described in PCT application WO99/30697 published on 14 Jun. 1998, the disclosures of which relating to α-adrenergic receptors are incorporated herein by reference and include, selective $\alpha_1$-adrenoceptor or $\alpha_2$-adrenoceptor blockers and non-selective adrenoceptor blockers, suitable $\alpha_1$-adrenoceptor blockers include: phentolamine, phentolamine mesylate, trazodone, alfuzosin, indoramin, naftopidil, tamsulosin, dapiprazoie, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $\alpha_2$-blocker blockers from U.S. Pat. No. 6,037,346 [14 Mar. 2000] dibenamine, tolazoline, trimazosin and dibenamine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; α$_2$-Adrenoceptor blockers include: clonidine, papaverine, papaverine hydrochloride, optionally in the presence of a cariotonic agent such as pirxamine;

3) NO-donor (NO-agonist) compounds. Suitable NO-donor compounds for use herein include organic nitrates, such as mono- di or tri-nitrates or organic nitrate esters including glyceryl trinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075;

4) Potassium channel openers or modulators. Suitable potassium channel openers/modulators for use herein include nicorandil, cromokalim, levcromakalim, lemakalim, pinacidil, cliazoxide, minoxidil, charybdotoxin, glyburide, 4-amini pyridine, BaCl$_2$;

5) Vasodilator agents. Suitable vasodilator agents for use herein include nimodepine, pinacidil, cyclandesate, isoxsuprine, chloroprumazine, halo peridol. Rec 15/2739, trazodone;

6) Thromboxane A2 agonists;

7) CNS active agents;

8) Ergot alkoloids; Suitable ergot alkaloids are described in U.S. Pat. No. 6,037,346 issued on 14 Mar. 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride;

9) Compounds which modulate the action of natruretic factors in particular atrial natruretic factor (also known as atrial naturetic peptide), B type and C type naturetic factors such as inhibitors or neutral endopeptidase;

10) Compounds which inhibit angiotensin-converting enzyme such as enapril, and combined inhibitors of angiotensin-converting enzyme and neutral endopeptidase such as omapatrilat.

11) Angiotensin receptor antagonists such as losartan:

12) Substrates for NO-synthase, such as L-arginine;

13) Calcium channel blockers such as amlodipine;

14) Antagonists of endothelin receptors and inhibitors or endothelin-converting enzyme;

15) Cholesterol lowering agents such as statins (e.g. atorvastatin/Lipitor-trade mark) and fibrates;

16) Antiplatelet and antithrombotic agents, e.g. tPA, uPA, warfarin, hirudin and other thrombin inhibitors, heparin thromboplastin activating factor inhibitors;

17) Insulin sensitising agents such as rezulin and hypoglycaemic agents such as glipizide;

18) L-DOPA or carbidopa;

19) Acetylcholinesterase inhibitors such as donezipil;

20) Steroidal or non-steroidal anti-inflammatory agents;

21) Estrogen receptor modulators and/or estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof the preparation of which is detailed in WO 96/21656;

23) A PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an IC50 against the respective enzyme of less than 100 nM (with the proviso that PDE 3 and 4 inhibitors are only administered topically or by injection to the penis);

22) Vasoactive intestinal protein (VIP), VIP mimetic, VIP analogue, more particularly mediated by one or more of the VIP receptor subtypes VPAC1, VPAC or PACAP (pituitary adenylate cyclase activating peptide), one or more of a VIP receptor agonist or a VIP analogue (e.g. Ro-125-1553) or a VIP fragment, one or more of a α-adrenoceptor antagonist with VIP combination (e.g. Invicorp, Aviptadil);

23) A melanocortin receptor agonist or modulator or melanocortin enhance, such as melanotan II, PT-14, PT-141 or compounds claimed in WO-09964002, WO-00074679, WO-09955679, WO-00105401, WO-00058361, WO-00114879, WO-00113112, WO-09954358;

24) A serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993;

25) A testosterone replacement agent (including dehydroandrostendione), testosternone (Tostrelle), dihydrotestosterone or a testosterone implant;

26) Estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone);

27) A modulator of transporters for noradrenaline, dopamine and/or serotonin, such as bupropion, GW-320659;

28) A purinergic receptor agonist and/or modulator;

29) A neurokinin (NK) receptor antagonist, including those described in WO-09964008;

30) An opioid receptor agonist, antagonist or modulator, preferably agonists for the ORL-1 receptor;

31) An agonist or modulator for oxytocin/vasopressin receptors, preferably a selective oxytocin agonist or modulator;

32) Modulators of cannabinoid receptors;

33) A SEP inhibitor (SEPi), for instance a SEPi having an IC$_{50}$ at less than 100 nanomotar, more preferably, at less than 50 nanomolar.

Preferably, the SEP inhibitors according to the present invention have greater than 30-fold, more preferably greater than 50-fold selectivity for SEP over neutral endopeptidase NEP EC 3.4.24.11 and angiotensin converting enzyme (ACE). Preferably the SEPi also has a greater than 100-fold selectivity over endothelin converting enzyme (ECE).

By cross reference herein to compounds contained in patents and patent applications which can be used in accordance with invention, we mean the therapeutically active compounds as defined in the claims (in particular of claim 1) and the specific examples (all of which is incorporated herein by reference).

If a combination of active agents is administered, then they may be administered simultaneously, separately or sequentially.

Auxiliary Agents—PDE5 Inhibitors

The suitability of any particular cGMP PDE5 inhibitor can be readily determined by evaluation of its potency and selectivity using literature methods followed by evaluation of its toxicity, absorption, metabolism, pharmacokinetics, etc in accordance with standard pharmaceutical practice.

IC50 values for the cGMP PDE5 inhibitors may be determined using the PDE5 assay (see hereinbelow).

Preferably the cGMP PDE5 inhibitors used in the pharmaceutical combinations according to the present invention are selective for the PDE5 enzyme. Preferably (when used orally) they are selective over PDE3, more preferably over PDE3 and PDE4. Preferably (when oral), the cGMP PDE5 inhibitors of the invention have a selectivity ratio greater than 100 more preferably greater than 300, over PDE3 and more preferably over PDE3 and PDE4.

Selectivity ratios may readily be determined by the skilled person. IC50 values for the PDE3 and PDE4 enzyme may be determined using established literature methodology, see S A Ballard et al, Journal of Urology, 1998, vol. 159, pages 2164-2171 and as detailed herein after.

Suitable cGMP PDE5 inhibitors for the use according to the present invention include:

the pyrazolo[4,3-d]pyrimidin-7-ones disclosed in EP-A-0463756; the pyrazolo[4,3-d]pyrimidin-7-ones disclosed in EP-A-0526004; the pyrazolo[4,3-d]pyrimidin-7-ones disclosed in published international patent application WO 93/06104; the isomeric pyrazolo[3,4-d]pyrimidin-4-ones disclosed in published international patent application WO 93/07149; the quinazolin-4-ones disclosed in published international patent application WO 93/12095; the pyrido [3,2-d]pyrimidin-4-ones disclosed in published international patent application WO 94/05661; the purin-6-ones disclosed in published international patent application WO 94/00453; the pyrazolo[4,3-d]pyrimidin-7-ones disclosed in published international patent application WO 98/49166; the pyrazolo[4,3-d]pyrimidin-7-ones disclosed in published international patent application WO99/54333; the pyrazolo[4,3-d]pyrimidin-4-ones disclosed in EP-A-0995751; the pyrazolo[4,3-d]pyrimidin-7-ones disclosed in published international patent application WO 00/24745; the pyrazolo[4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124. The pyrazolo[4,3-d]pyrimidin-7-ones disclosed in published international application WO 01/27112; the pyrazolo[4,3-d]pyrimidin-7-ones disclosed in published international application WO 01/27113; the compounds disclosed in EP-A-1092718 and the compounds disclosed in EP-A-1092719.

Further suitable PDE5 inhibitors for the use according to the present invention include:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978 as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotelia D P, J. Med. Chem., 2000, 43, 1257.

Still other suitable PDE5 inhibitors include:

4-bromo-5-(pyridylmethylamino)-6-[3-(4-chlorophenyl)-propoxy]-3-(2H)pyridazinone; 1-[4-[(1,3-benzodioxol-5-ylmethyl)amiono]-6-chloro-2-quinozolinyl]-4-piperidine-carboxylic acid, monosodium salt, (+)-cis-5,6a,7,9,9,9a-hexahydro-2-[4-(trifluoro methyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough), GF-196960 (Glaxo Wellcome), E-8010 and E-4010 (Eisai); Bay-38-3045 & 38-9456 (Bayer) and Sch-51866.

The compounds of the formula (I) can be administered alone but will generally be administered in admixture with a suitable pharmaceutical excipient, diluent or carrier selected with regard to the intended route of administration and standard pharmaceutical practice.

Accordingly the present invention provides for a composition comprising a compound of formula (I), (Ia) or (Ib) and a pharmaceutically acceptable diluent or carrier.

For example, the compounds of the formula (I), (Ia) or (Ib) can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC) hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fitters in gelatin capsules. Preferred excipients in this regard include lactose, starch, a cellulose, milk sugar or high molecular weight polyethylene glycols. For aqueous suspensions and/or elixirs, the compounds of the formula (I), (Ia) or (Ib) may be combined with various sweetening or flavouring agents, colouring matter or dyes, with emulsifying and/or suspending agents and with diluents such as water, ethanol, propylene glycol and glycerin, and combinations thereof.

The compounds of the formula (I), (Ia) or (Ib) can also be administered parenterally, for example, intravenously, intraarterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds of formula (I), (Ia) or (Ib) can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), (Ia) or (Ib), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the compound of the invention, a suitable powder base such as lactose or starch and a performance modifier such as i-leucine, mannitol, or magnesium stearate.

Formulations for inhaled/intranasal administration may be formulated to be immediate and/or modified release.

Alternatively, the compounds of the formula (I), (Ia) or (Ib) can be administered in the form of a suppository or pessary, or they may be applied topically in the form of a gel, hydrogel, lotion, solution, cream, ointment or dusting powder. The compounds of the formula (I), (Ia) or (Ib) may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I), (Ia) or (Ib) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I), (Ia) or (Ib) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The present invention is further exemplified by the following, non-limiting examples:

The invention is illustrated by the following non-limiting examples in which the following abbreviations and definitions are used:

$\alpha_D$ optical rotation at 587 nm,

Arbace® filter agent b broad
Boc tert-butoxycarbonyl
CDCl$_3$ chloroform-d1
CD$_3$OD methanol-d4
δ chemical shift
d doublet
dd double doublet
DCM dichloromethane
DMF N,N-dimethylformamide
DMSO dimethylsulfoxide
h hours
HCl hydrogen chloride
LRMS low resolution mass spectrum
m multiplet
m/z mass spectrum peak
min minutes
Mpt melting point
NaOH sodium hydroxide
NMR nuclear magnetic resonance
q quartet
s singlet
t triplet
Tf trifluoromethanesulfonyl
TFA trifluoroacetic acid
THF tetrahydrofuran
TLC thin layer chromatography Melting points were determined using a Perkin Elmer DSC7 at a heating rate of 20° C./minute).

X-RAY DIFFRACTION DATA WERE RECORDED AT ROOM TEMPERATURE USING A BRUKER AXS SMART-APEX CCD AREA-DETECTOR DIFFRACTOMETER (MO Kα RADIATION). INTENSITIES WERE INTEGRATED FROM SEVERAL SERIES OF EXPOSURES. EACH EXPOSURE COVERED 0.3° IN ω, WITH AN EXPOSURE TIME OF 60 S AND THE TOTAL DATA SET WAS MORE THAN A SPHERE.

EXAMPLE 1

2-Amino-1-(3-methoxyphenyl)ethanol

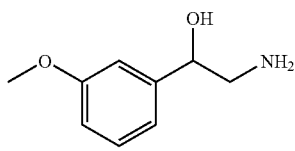

3-Methoxybenzaldehyde (27.2 g, 0.2 mol) in THF (150 ml) was added to a stirred solution of 3N HCl (aq) (150 ml, 0.3 mol) and sodium sulphite (37.8 g, 0.3 mol) at room temperature. After 10 minutes potassium cyanide (19.53 g, 0.3 mol) was added, portion wise, and the reaction mixture was then stirred for 30 minutes. Diethyl ether (800 ml) and water (300 ml) were added and subsequent layers portioned. Aqueous re-extracted with diethyl ether (50 ml) the organics combined, dried over anhydrous magnesium sulphate, filtered then concentrated in vacuo to give the cyanohydrin intermediate as a colourless oil, (35.57 g, 0.22 mol, >100%). Borane-tetrahydrofuran complex (1M in THF) (400 ml, 0.4 mol) was then cautiously added to the cyanohydrin in THF (100 ml). Once effervescence had ceased, stirring was continued at reflux for 1.5 hours under an atmosphere of nitrogen. The reaction mixture was cooled then quenched with methanol (40 ml) before concentrating in vacuo to give a colourless oil. 6M HCl (aq) (200 ml) was added and reaction stirred at reflux for two hours before concentrating in vacuo to give a white solid. This was pre-absorbed onto silica then purified by column chromatography eluting with dichloromethane: methanol:ammonia (90:10:1) to give the title compound as a colourless oil (31.3 g, 0.19 mol, 94%). $^1$H NMR (CDCl$_3$, 400 MHz) δ: 1.60 (bs, 2H), 2.80 (dd, 1H), 3.02 (dd, 1H), 3.46 (s, 1H), 3.81 (s 3H), 4.60 (dd, 1H), 6.81 (d, 1H), 6.91 (d, 1H), 6.93 (s, 1H), 7.22 (t, 1H). LRMS: m/z 168 (M-H$^+$). Analysis found C, 56.66; H, 8.28; N, 6.91%. C$_9$H$_{13}$NO$_2$1.33H$_2$O requires C, 56.33; H, 8.27; N, 7.30%.

EXAMPLE 2

N-[2-Hydroxy-2-(3-methoxyphenyl)ethyl]propionamide

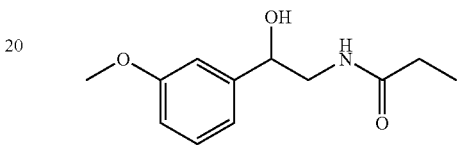

Triethylamine (52 ml, 0.37 mol) was added to the amine from example 1 (31.3 g, 0.19 mol) in dichloromethane (400 ml) and reaction mixture stirred under an atmosphere of nitrogen gas at 0° C. for 10 minutes. Propionyl chloride (16.3 ml, 0.19 mol) was added and after stirring for 30 minutes, the reaction temperature was raised to room temperature for a further 5 hours. The reaction mixture was quenched 1N HCl (aq) (100 ml) and then extracted with dichloromethane (2×50 ml). The organic fractions were combined, dried over anhydrous magnesium sulphate, filtered and concentrated in vacuo to give the title compound as a colourless oil that crystallised on standing to white crystals (28 g, 0.13 mol, 67%). $^1$H NMR (CDCl$_3$, 400 MHz) δ: 1.18 (t, 3H), 2.22 (q, 2H), 2.51 (bs, 1H), 3.31 (m, 1H), 3.71 (dd, 1H), 3.80 (s, 3H), 4.81 (m, 1H), 5.95 (bs, 1H), 6.80 (d 1H), 6.90 (d 1H), 6.91 (s, 1H), 7.22 (t, 1H). LRMS: m/z 224. Mpt: 77-78° C. Analysis found C, 63.86; H, 7.82; N, 6.28%. C$_{12}$H$_{17}$NO$_3$0.1H$_2$O requires C, 64.04; H, 7.70; N, 6.22%.

EXAMPLE 3

1-(3-Methoxyphenyl)-2-propylaminoethanol

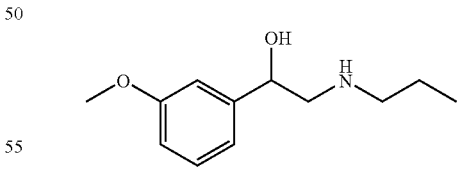

Borane-tetrahydrofuran complex (1M in THF) (376 ml, 0.4 mol) was added to amide from example 2 (28 g, 0.13 mol) in dry THF (100 ml) then the reaction mixture, stirred under an atmosphere of nitrogen gas, was brought to reflux for 2.5 hours. The reaction mixture was cooled then quenched with methanol (40 ml), before concentrating in vacuo to give an opaque white oil. 6N HCl (aq) (200 ml) was added and reaction stirred at reflux for two hours. The reaction mixture was cooled then dichloromethane (200 ml) added and the layers separated. The aqueous layer was rendered basic by addition of potassium carbonate then re-extracted with dichloromethane (2×200 ml). Organic extracts were combined, dried over anhydrous magnesium sulphate, filtered and concentrated in vacuo to give the title compound as a colourless oil that crystallised on standing to give colourless crystals (15.3 g, 0.07 mol, 59%). $^1$H NMR (CDCl$_3$, 400 MHz) δ: 0.93 (t, 3H), 1.62 (q, 2H), 2.71 (q, 2H), 2.81 (t, 2H), 3.00 (d, 1H), 3.80 (s, 3H), 4.30 (bs, 1H), 4.89 (d, 1H), 6.81 (d, 1H), 6.91 (d, 1H), 6.93 (s, 1H), 7.22 (t, 1H). LRMS: m/z 210. Mpt; 50-51° C. Analysis found C, 67.47; H, 9.02; N, 6.45%. C$_{12}$H$_{19}$NO$_2$.0.2H$_2$O requires C, 67.70; H, 9.19; N, 6.58%.

EXAMPLE 4

2-Chloro-N-[2-hydroxy-2-(3-methoxyphenyl)ethyl]-N-propylacetamide

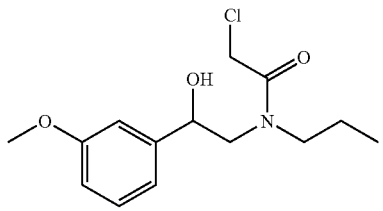

Sodium hydroxide (15.1 g, 0.38 mol) in water (180 ml) was added to the amine from example 3 (15.8 g, 0.08 mol) in dichloromethane (500 ml) and the solution vigorously stirred at room temperature. Chloroacetylchloride (7.22 ml, 0.09 mol) was then added and the reaction mixture stirred for a further 30 minutes. The layers were separated and the aqueous layer re-extracted with dichloromethane (200 ml). The organic extracts were combined, dried over anhydrous magnesium sulphate, filtered and concentrated in vacuo to give the title compound as a colourless oil (17.8 g, 0.06 mol, 83%). $^1$H NMR (CDCl$_3$ 400 MHz) δ: 0.96 (t, 3H), 1.62 (q, 2H), 3.21 (q, 2H), 3.57-3.71 (m, 2H), 3.82 (s, 3H), 4.01-4.21 (bq, 1H), 4.16 (s, 2H), 5.00 (m, 1H), 6.82 (m, 1H), 6.91-6.99 (m, 2H), 7.22 (m, 1H). LRMS: m/z 286. Analysis found C, 57.38; H, 6.95; N, 4.67%. C$_{14}$H$_{20}$NO$_3$Cl.0.33H$_2$O requires C, 57.64; H, 7.14; N, 4.80%.

EXAMPLE 5

6-(3-Methoxyphenyl)-4-propylmorpholin-3-one

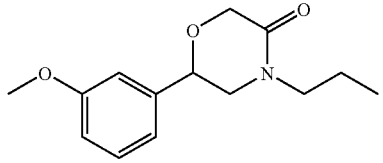

Potassium hydroxide (4.2 g, 0.07 mol), isopropyl alcohol (500 ml) and the amide from example 4 (17.8 g, 0.06 mol) were stirred together as an opaque solution with water (15 ml) for 2 hours. The reaction mixture was concentrated in vacuo and the yellow residue dissolved in ethyl acetate (200 ml). This was partitioned with water (200 ml) then brine (200 ml). The organic fraction was dried over anhydrous magnesium sulphate, filtered and concentrated in vacuo to give the title compound as a yellow oil (15.8 g, 0.06 mol, 100%). $^1$H NMR (CDCl$_3$, 400 MHz) δ: 0.96 (t, 3H), 1.62 (m, 2H), 3.36 (m, 2H), 3.51 (q, 2H), 3.81 (s, 3H), 4.30-4.62 (bq, 2H), 4.79 (d, 1H), 6.85 (d, 1H), 6.91 (d, 1H), 6.95 (s, 1H), 7.29 (t, 1H). LRMS: m/z 272. Analysis found C, 66.80; H, 7.78; N, 5.52%. C$_{14}$H$_{19}$NO$_3$.0.1H$_2$O requires C, 66.96; H, 7.71; N, 5.58%.

EXAMPLE 6

2-(3-Methoxyphenyl)-4-propylmorpholine

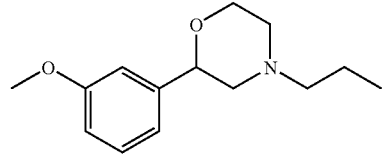

Borane-tetrahydrofuran complex (1M in THF) (200 ml, 0.19 mol) was added dropwise to the morpholin-3-one from example 5 (15.8 g, 0.06 mol) in dry THF (100 ml) under an atmosphere of nitrogen, over 30 minutes. The reaction mixture was brought to reflux for 3 hours then cooled and quenched by addition of methanol (30 ml). The reaction mixture was then concentrated in vacuo and the colourless residue cautiously suspended in 4N HCl (aq) (400 ml) before refluxing for 2.5 hours. The reaction mixture was cooled and dichloromethane (200 ml) added. Layers were separated and the aqueous layer rendered basic by addition of potassium carbonate before re-extracting with dichloromethane (3×100 ml). The organic extracts were combined, dried over anhydrous magnesium sulphate, filtered and concentrated in vacuo to give the title compound as a colourless oil (12.51 g, 0.05 mol, 84%). $^1$H NMR (CDCl$_3$, 400 MHz) δ: 0.95 (t, 3H), 1.59 (q, 2H), 2.05 (t, 1H), 2.23 (t, 1H), 2.40 (t, 2H), 2.81 (d,1H), 2.98 (d1H), 3.80 (s, 3H), 3.85 (t, 1H), 4.05 (d, 1H), 4.60 (d, 1H), 6.81 (d, 1H), 6.91 (d, 1H), 7.21 (t, 1H), 7.23 (s, 1H). LRMS: m/z 236. Analysis found C, 68.94; H, 8.80; N, 5.79%. C$_{14}$H$_{21}$NO$_2$.0.5H$_2$O requires C, 68.82; H, 9.08; N, 5.73%.

EXAMPLE 7A

R-(−)-3-(4-Propylmorpholin-2-yl)phenol

EXAMPLE 7B

S-(+)-3-(4-Propylmorpholin-2-yl)phenol

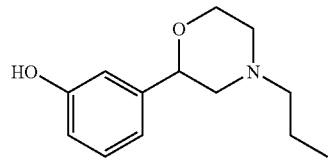

Hydrobromic acid (250 ml) and the anisole from example 6 (8.62 g, 0.03 mol) were heated to reflux together for 1 hour. After cooling the reaction mixture was diluted with water (100 ml) then neutralised by addition of NH$_4$OH (20 ml). The yellow opaque solution was then extracted with dichloromethane (2×100 ml). The organic extracts were combined then dried over anhydrous magnesium sulphate, filtered and concentrated in vacuo to give the racemic mixture of the title compound as a yellow oil (7.78 g, 0.03 mol, 96%). The enantiomers were separated by chiral chromatography (Chiralpak AD 250*20 mm column) eluting with hexane:isopropyl alcohol:diethylamine (70:30:0.05) to give enantiomer 1 (ee>99.5%) and enantiomer 2 (ee>99%). Each enantiomer was purified by column chromatography on silica eluting with dichloromethane:methanol (95:5) to give enantiomer 1 (7a) (3.02 g, 0.014 mol, 39%) and enantiomer 2 (7b) (3.15 g, 0.014 mol, 40%) as colourless oils. Enantiomer 1

(7a): ¹H NMR (CDCl₃, 400 MHz) δ: 0.96 (t, 3H), 1.60 (q, 2H), 2.13 (t, 1H), 2.31 (t, 1H), 2.41 (t, 2H), 2.85 (d, 1H), 3.02 (d, 1H), 3.90 (t, 1H), 4.02 (dd, 1H), 4.60 (d, 1H), 6.78 (d, 1H), 6.80 (s, 1H), 6.91 (d, 1H), 7.20 (t, 1H). LRMS: m/z 222 (M-H⁺). Enantiomer 2 (7b): ¹H NMR (CDCl₃, 400 MHz) δ: 0.96 (t, 3H), 1.60 (q, 2H), 2.13 (t, 1H), 2.31 (t, 1H), 2.41 (t, 2H), 2.85 (d, 1H), 3.02 (d, 1H), 3.90 (t, 1H), 4.02 (dd, 1H), 4.60 (d, 1H), 6.78 (d, 1H), 6.80 (s, 1H), 6.91 (d, 1H), 7.20 (t, 1H). LRMS: m/z 222 (M-H⁺).

EXAMPLE 8

R-(−)-3-(4-Propylmorpholin-2-yl)phenol hydrochloride

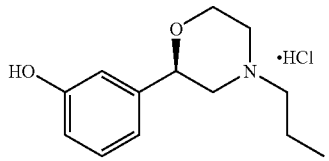

Enantiomer 1 (7a) of example 7 (3.00 g, 0.014 mol) was dissolved in diethyl ether (180 ml) and hydrogen chloride (2.0 M solution in diethyl ether) (10 ml) was added. The reaction mixture was stirred at room temperature for 30 minutes, then the solvent was decanted and dried in vacuo, giving title compound as a white solid (3.115 g, 0.012 mol, 90%). ¹H NMR (CD₃OD, 400 MHz) δ: 1.06 (t, 3H), 1.81 (m, 2H), 3.02 (t, 1H), 3.16 (t, 2H), 3.20 (t, 1H), 3.60 (t, 2H), 4.01 (t, 1H), 4.26 (d, 1H), 4.71 (d, 1H), 6.78 (d, 1H), 6.82 (s, 1H), 6.83 (d 1H), 7.21 (t, H). LRMS: m/z 222 (M-H⁺). Analysis found C, 59.74; H, 7.98; N, 5.25%. $C_{13}H_{19}NO_2 \cdot 0.18H_2O$ requires C, 59.82; H, 7.86; N, 5.37%, $\alpha_D = -5.66°$ (Methanol 10.6 mg/10 ml).

A SAMPLE OF THE TITLE COMPOUND WAS RE CRYSTALLISED BY VAPOUR DIFFUSION USING A METHANOL: DIETHYL ETHER MIX AND AN X-RAY CRYSTAL STRUCTURE OBTAINED. THE ABSOLUTE STEREOCHEMISTRY OF THE TITLE COMPOUND WAS DETERMINED FROM THE DIFFRACTION DATA BY THE METHOD OF FLACK[1] AND WAS SHOWN TO HAVE AN 'R' CONFIGURATION.

REF 1: H. D. FLACK, *ACTA CRYST.* 1983, 439, 876-881

EXAMPLE 9

2-Amino-1-(3,5-dimethoxyphenyl)ethanol

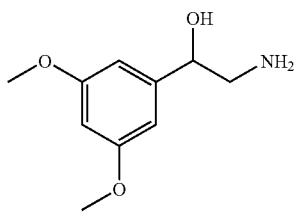

Prepared following the same method as for example 1 starting from 3,5-dimethoxybenzaldehyde (5.00 g, 0.03 mol). After refluxing in 6M HCl (aq) the reaction mixture was cooled and extracted with diethyl ether (2×80 ml). The organic layers were discarded and the aqueous layer basified by the addition of potassium carbonate. The aqueous residue was then extracted with ethyl acetate (3×70 ml). The organic extracts were combined and dried over anhydrous magnesium sulphate, filtered and concentrated in vacuo to give the title compound as a pale yellow oil (3.47 g, 0.018 mmol, 59%). ¹H NMR (CD₃OD, 400 MHz) δ: 2.77-2.86 (m, 2H), 3.78 (s, 6H), 4.60 (m, 1H), 6.38 (s, 1H), 6.52 (s, 2H). LRMS: m/z 198 (M-H⁺).

EXAMPLE 10

N-[2-(3,5-dimethoxyphenyl)-2-hydroxyethyl]propionamide

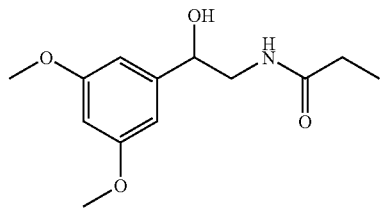

Prepared following the same method as for example 2 starting from the amine in example 9 (3.41 g, 0.017 mol). The crude reaction mixture was purified by column chromatography on silica eluting with dichloromethane:methanol (95:5) to give the title compound as a bright yellow oil (3.08 g, 0.012 mol, 70%). ¹H NMR (CDCl₃, 400 MHz) δ: 1.18 (m, 3H), 2.24 (m, 2H), 3.34 (m, 1H), 3.68 (m, 1H), 3.81 (s, 6H), 4.80 (dd, 1H), 5.95 (bs; 1H), 6.39 (s, 1H), 6.51 (s, 2H). LRMS: m/z 252 (M-H⁻).

EXAMPLE 11

1-(3,5-dimethoxyphenyl)-2-propylaminoethanol

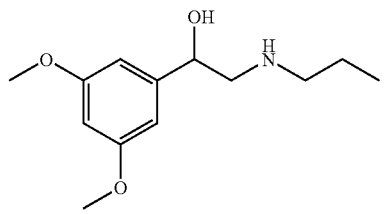

Prepared following the method as for example 3 starting from the amide in example 10 (3.06 g, 0.012 mol) to give the title compound as an orange oil (2.72 g, 0.011 mol, 94%). ¹H NMR (CD₃OD, 400 MHz) δ: 0.95 (t, 3H), 1.56 (m, 2H), 2.61 (m, 2H), 2.77 (d, 2H), 3.78 (s, 6H), 4.70 (t, 1H), 6.38 (s, 1H), 6.51 (s, 2H). LRMS: m/z 240 (M-H⁺).

EXAMPLE 12

2-Chloro-N-[2-(3,5-dimethoxyphenyl)-2-hydroxyethyl]-N-propylacetamide

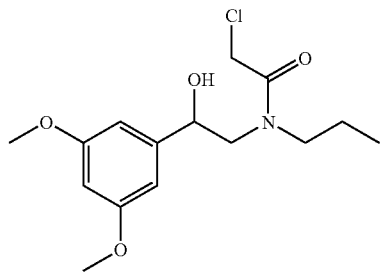

Prepared following the same method as for example 4 starting from the amine in example 11 (2.70 g, 0.011 mol) to give the title compound as a yellow oil (3.56 g, 0.011 mol, 100%). ¹H NMR (CDCl₃, 400 MHz) δ: 0.92 (t, 3H), 1.61 (m, 2H), 3.20 (m, 2H), 3.51-3.64 (m, 2H), 3.80 (d, 6H), 4.13 (s, 2H), 4.95 (m, 1H), 6.40 (m, 1H), 6.55 (s, 2H). LRMS: m/z 316 (M-H⁺).

EXAMPLE 13

6-(3,5-Dimethoxyphenyl)-4-propylmorpholin-3-one

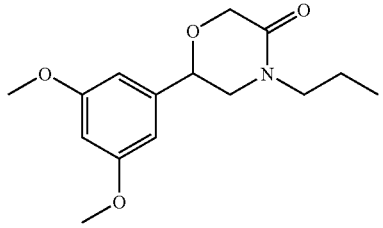

Prepared following the same method as for example 5 starting from the amide in example 12 (3.54 g, 0.011 mol) to give the title compound as a yellow oil (2.44 g, 0.009 mol, 78%). ¹H NMR (CDCl₃, 400 M Hz) 0.94 (t, 3H), 1.61 (m, 2H), 3.30 (m, 2H), 3.49 (m, 2H), 3.80 (s, 6H), 4.30 (d, 1H), 4.42 (d, 1H), 4.73 (dd, 1H), 6.42 (s 1H), 6.53 (s, 2H). LRMS: m/z 280 (M-H⁺).

EXAMPLE 14

2-(3,5-Dimethoxyphenyl)-4-propylmorpholine

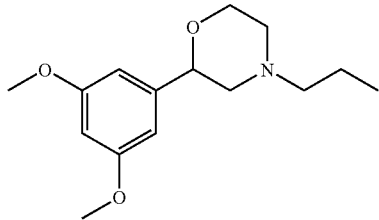

Prepared following the method as for example 6 starting from the amide in example 13 (2.42 g, 0.009 mol). After refluxing in 6M HCl (aq) the cooled reaction mixture was extracted with diethyl ether (2×80 ml. The organic layers were discarded and the aqueous basified by addition of potassium carbonate. The aqueous residue was then extracted with ethyl acetate (3×80 ml) and the organic extracts combined, dried over anhydrous magnesium sulphate, filtered then concentrated in vacuo to give the title compound as a pale orange oil (2.14 g, 0.008 mol, 93%). ¹H NMR (CD₃OD, 400 MHz) δ: 0.95 (t, 3H), 1.58 (m, 2H), 2.01 (m, 1H), 2.22 (dt, 1H), 2.38 (t, 2H), 2.83 (d, 1H), 2.93 (d, 1H), 3.78 (m, 7H), 4.01 (dd, 1H), 4.45 (dd, 1H), 6.39 (s, 1H), 6.49 (s, 2H). LRMS: m/z 266 (M-H⁺).

EXAMPLE 15A

R-5-(4-Propylmorpholin-2-yl)benzene-1,3-diol

EXAMPLE 15B

S-5-(4-Propylmorpholin-2-yl)benzene-1,3-diol

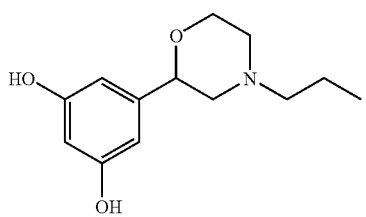

Prepared following the same route as for example 7 starting from the 3,5-dimethoxyphenyl compound in example 14 (1.00 g, 0.004 mol) giving the title racemic compound as a brown oil (145 mg, 0.61 mmol, 16%). The enantiomers were separated by chiral chromatography (Chiralpak AD 250*20 mm column) eluting with hexane:isopropyl alcohol: (80:20) to give enantiomer 1 (15a) (5.2 mg) (ee>98.94%) and enantiomer 2 (15b) (5.1 mg) (ee>96.46%) as brown oils. Enantiomer 1 (15a): ¹H NMR (CD₃OD, 400 MHz) δ: 0.96 (t, 3H), 1.58 (m, 2H), 2.01 (t, 1H), 2.20 (dt, 1H), 2.37 (t, 2H), 2.81-2.92 (m, 2H), 3.89 (dt, 1H), 3.99 (dd, 1H), 4.38 (dd, 1H), 6.18 (t, 1H), 6.26 (s, 2H). LRMS: m/z 238 (M-H⁺). Enantiomer 2 (15b): ¹H NMR (CD₃OD, 400 MHz) δ: 0.95 (t, 3H), 1.58 (m, 2H), 2.01 (t, 1H), 2.20 (dt, 1H), 2.38 (t, 2H), 2.80-2.92 (q, 2H), 3.78 (dt, 1H), 3.98 (dd, 1H), 4.38 (dd, 1H), 6.18 (s 1H), 6.25 (s, 2H). LRMS: m/z 238 (M-H⁺).

EXAMPLE 16

4-Fluoro-3-methoxybenzaldehyde

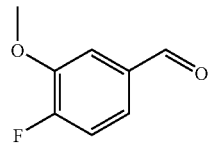

(4-Fluoro-3-methoxyphenyl)methanol (5.00 g, 0.03 mol) and manganese dioxide (33.4 g, 0.38 mol) were stirred in dichloromethane (100 ml) under an atmosphere of nitrogen, at gentle reflux for 16 hours. The cooled reaction mixture was then filtered through arbacel and concentrated in vacuo to give the title compound as a white solid (4.18 g, 0.027 mol, 85%). ¹H NMR (CDCl₃, 400 MHz) δ: 3.96 (s, 3H), 7.23 (d, 1H), 7.43 (m, 1H), 7.50 (d, 1H), 9.91 (s, 1H). Mpt: 61-63° C. Analysis found C, 62.18; H, 4.54%. C₈H₇FO₂ requires C, 62.34; H, 4.58%.

EXAMPLE 17

2-Amino-1-(4-fluoro-3-methoxyphenyl)ethanol

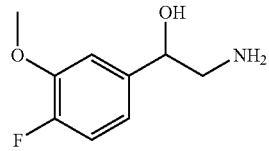

Prepared following the same method as for example 1 starting from 4-fluoro-3-methoxybenzaldehyde (4.17 g, 0.03 mol). After refluxing in 6M HCl (aq) the reaction mixture was cooled and extracted with diethyl ether (2×60 ml). The organic layers were discarded and the aqueous layer basified by the addition of potassium carbonate. The aqueous residue was then extracted with ethyl acetate (3×80 ml). The organic extracts were combined and dried over anhydrous magnesium sulphate, filtered and concentrated in vacuo to give the title compound as an orange oil (2.36 g, 0.013 mol, 47%). ¹H NMR (CD₃OD, 400 MHz) δ: 2.80-2.91 (m, 2H), 3.86 (s, 3H), 4.64 (m, 1H), 6.89 (m, 1H), 7.03 (t, 1H), 7.11 (dd, 1H). LRMS: m/z 186 (M-H⁺).

EXAMPLE 18

N-[2-(4-Fluoro-3-methoxyphenyl)-2-hydroxyethyl]-propionamide

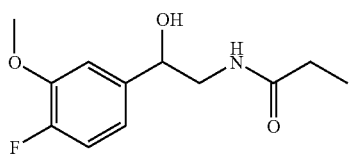

Prepared following the same method as for example 2 starting with the amine from example 17 (1.32 g, 0.007 mol). The crude reaction mixture was purified by column chromatography on silica eluting with ethyl acetate:pentane (2:1) to give the title compound as a yellow oil that crystallised on standing (0.59 g, 0.002 mol, 35%). $^1$H NMR (CDCl$_3$, 400 MHz) δ: 1.18 (t, 3H), 2.24 (q, 2H), 2.58 (bs, 1H), 3.34 (m, 1H), 3.63 (m, 1H), 3.88 (s, 3H), 4.82 (dd, 1H), 5.98 (bs, 1H), 6.82 (m, 1H), 7.01 (m, 2H). LRMS: m/z 242 (M-H$^+$).

EXAMPLE 19

1-(4-Fluoro-3-methoxyphenyl)-2-propylaminoethanol

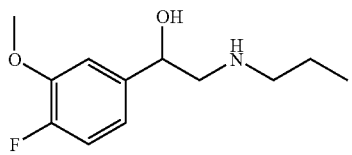

Prepared following the same method as for example 3 starting with the amide from example 18 (585 mg, 2.42 mmol). After refluxing in 6M HCl (aq) the reaction mixture was cooled and extracted with diethyl ether (2×50 ml). The organic layers were discarded and the aqueous layer basified by the addition of potassium carbonate. The aqueous residue was then extracted with ethyl acetate (3×50 ml). The organic extracts were combined and dried over anhydrous magnesium sulphate, filtered and concentrated in vacuo to give the title compound as a pale yellow oil (448 mg, 1.97 mmol, 81%), $^1$H NMR (CD$_3$OD, 400 MHz) δ: 0.96 (t, 3H), 1.58 (m, 2H), 2.63 (m, 2H), 2.79 (d, 2H), 3.96 (s, 3H), 4.77 (t, 1H), 6.90 (m, 1H), 7.03 (t, 1H), 7.11 (d, 1H). LRMS: m/z 228 (M-H$^+$).

EXAMPLE 20

2-Chloro-N-[2-(4-fluoro-3-methoxyphenyl)-2-hydroxyethyl]-N-propylacetamide

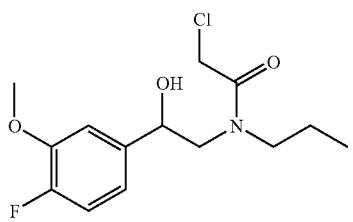

Prepared following the same method as for example 4 starting with the amine from example 19 (0.84 g, 4.00 mmol) to give the title compound as a yellow oil (0.97 g, 3.00 mmol, 87%). LRMS: m/z 304 (M-H$^+$). This was taken on crude.

EXAMPLE 21

6-(4-Fluoro-3-methoxyphenyl)-4-propylmorpholin-3-one

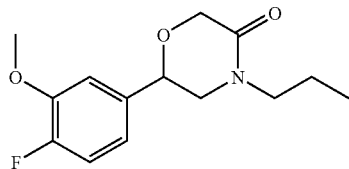

Prepared following the same method as for example 5 starting with the amide from example 20 (0.96 g, 3.00 mmol) to give the title compound as a yellow oil (0.64 g, 2.40 mmol, 75%). $^1$H NMR (CDCl$_3$, 400 MHz) δ: 0.94 (t, 3H), 1.62 (m, 2H), 3.33 (m, 2H), 3.48 (m, 2H), 3.91 (s, 3H), 4.34 (d, 1H), 4.43 (d, 1H), 4.76 (dd, 1H), 6.85 (m, 1H), 7.01-7.08 (m, 2H). LRMS: m/z 268 (M-H$_+$).

EXAMPLE 22

2-(4-Fluoro-3-methoxyphenyl)-4-propylmorpholine

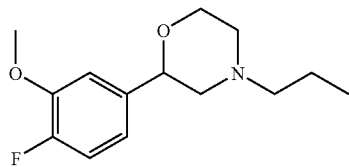

Prepared following the same method as for example 6 starting with the morpholin-3-one from example 21 (633 mg, 2.37 mmol). After refluxing in 6M HCl (aq) the reaction mixture was cooled and extracted with diethyl ether (2×20 ml). The organic layers were discarded and the aqueous layer basified by the addition of potassium carbonate. The aqueous residue was then extracted with ethyl acetate (3×20 ml). The organic extracts were combined and dried over anhydrous magnesium sulphate, filtered and concentrated in vacuo to give the title compound as a yellow oil (552 mg, 2.18 mmol, 92%). $^1$H NMR (CD$_3$OD, 400 MHz) δ: 0.95 (t, 3H), 1.58 (m, 2H), 2.02 (t, 1H), 2.22 (dt, 1H), 2.38 (t, 2H), 2.85 (d, 1H), 2.93 (d, 1H), 3.80 (m, 1H), 3.84 (s, 3H), 4.01 (dd, 1H), 4.50 (dd, 1H), 6.88 (m, 1H), 7.02 (t, 1H), 7.09 (d, 1H). LRMS: m/z 254 (M-H$^+$).

EXAMPLE 23A

R-(+)-2-Fluoro-5-(4-propylmorpholin-2-yl)phenol

EXAMPLE 23B

S-(-)-2-Fluoro-5-(4-propylmorpholin-2-yl)phenol

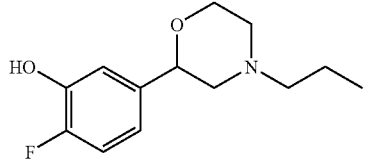

Prepared following the same method as for example 7 starting with the anisole from example 22 (200 mg, 0.789 mmol). The crude reaction mixture was purified by column chromatography on silica eluting with dichloromethane:methanol (90:10) to give the title racemic compound as a dark yellow viscous oil (149 mg, 0.62 mmol, 79%). The enantiomers were separated by chiral chromatography (Chiralpak AD 250*20 mm column) eluting with hexane:isopropyl alcohol: (90:10) to give enantiomer 1 (23a) as an opaque oil (15 mg) (ee>99.5%) and enantiomer 2 (23b) as a crystalline solid (16 mg) (ee>99%). Enantiomer 1 (23a): $^1$H NMR (CD$_3$OD, 400 MHz) δ: 0.95 (t, 3H), 1.58 (m, 2H), 2.01 (t, 1H), 2.21 (dt, 1H), 2.37 (t, 2H), 2.82-2.97 (bq, 2H), 3.78 (dt, 1H), 3.99 (dd, 1H), 4.43 (d, 1H), 6.78 (m, 1H), 6.89-7.01 (m, 2H). LRMS: m/z 240 (M-H$^+$). α$_D$+0.91 (Ethanol 1.10 mg/ml). Enantiomer 2 (23b): $^1$H NMR (CD$_3$OD, 400 MHz) δ: 0.96 (t, 3H), 1.58 (m, 2H), 2.01 (t, 1H), 2.22 (dt, 1H), 2.38 (t, 2H), 2.78 (dd, 2H), 3.78 (dt, 1H), 4.00 (dd, 1H), 4.43 (dd, 1H), 6.78 (m, 1H), 6.91 (d, 1H), 6.98 (t, 1H). LRMS: m/z 240 (M-H$^+$). α$_D$=−0.40 (Ethanol 1.00 mg/ml).

EXAMPLE 24

2-Amino-1-(4-benzyloxyphenyl)ethanol

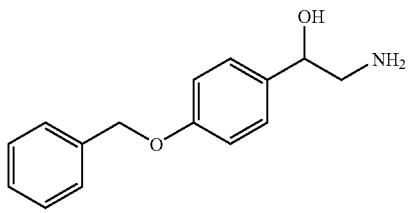

Potassium cyanide (20.15 g, 0.31 mol) and ammonium chloride (16.4 g, 0.31 mol) were dissolved in water (60 ml) to which was added 4-benzyloxybenzaldehyde (32.9 g, 0.155 mol) followed by diethyl ether (100 ml). The reaction mixture was stirred vigorously for 48 hours at room temperature before extracting with ethyl acetate (2×200 ml). The combined organic layers were dried over anhydrous magnesium sulphate, filtered and concentrated in vacuo to give the cyanohydrin intermediate as a yellow solid (34.2 g, 0.14 mol, 90%). The cyanohydrin was then dissolved in dry THF (300 ml) and borane-methyl sulphide complex (26.6 ml, 0.28 mol) was added. The reaction mixture was refluxed for 2 hours before being quenched with methanol (50 ml). Water (50 ml) was added followed by c.HCl (40 ml) and the reaction mixture was stirred for 2 hours until the exotherm subsided. The reaction mixture was then concentrated in vacuo and the residue diluted with water (100 ml). The aqueous solution was then basified by addition of NH$_4$OH (30 ml), and extracted with ethyl acetate (3×150 ml). The organic extracts were dried over anhydrous magnesium sulphate, filtered and concentrated in vacuo to give the title compound as a white solid (24.8 g, 0.10 mol, 73%). $^1$H NMR (CDCl$_3$, 400 MHz) δ: 1.62 (bs, 3H), 2.81 (dd, 1H), 2.99 (d, 1H), 4.61 (q, 1H), 5.07 (s, 2H), 6.95 (d, 2H), 7.22-7.45 (m, 7H). LRMS: m/z 244 (M-H$^+$).

EXAMPLE 25

N-[2-(4-BENZYLOXYLPHENYL)-2-HYDROXY-ETHYL)PROPIONAMIDE

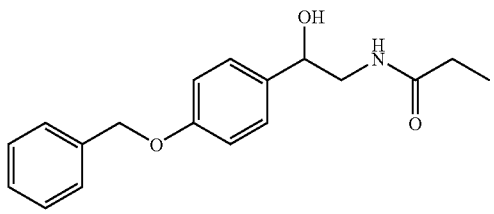

The amine from example 24 (24.8 g, 0.10 mol) was dissolved in dichloromethane (700 ml) and to this was added triethylamine (20.86 ml, 0.15 mol). The reaction mixture was stirred and cooled to 0° C., before propionyl chloride (7.12 ml, 0.082 mol) was added dropwise. The reaction mixture was then allowed to warm to room temperature over 16 hours before quenching with 3M HCl (aq) (20 ml) and water (100 ml). The reaction mixture was then extracted with dichloromethane (3×200 ml) and the combined organic layers dried over anhydrous magnesium sulphate, filtered and concentrated in vacuo to give the title compound as a clear viscous gum (27.5 g, 0.092 mol, 90%). $^1$H NMR (CDCl$_3$, 400 MHz) δ: 1.10 (t, 3H), 2.19 (q, 2H), 3.32-3.43 (m, 4H), 4.81 (s, 2H), 5.11 (m, 1H), 6.99 (d, 2H), 7.25-7.42 (m, 7H). LRMS: m/z 298 (M-H$^-$).

EXAMPLE 26

1-(4-benzyloxyphenyl)-2-propylaminoethanol

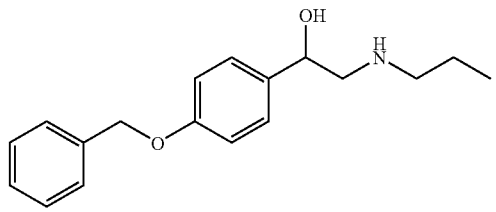

To the amide from example 25 (27.5 g, 0.092 mol) in dry THF (100 ml) was added borane-methyl sulphide complex (17.5 ml, 0.18 mol) and the reaction mixture was stirred at reflux for 2 hours. The reaction mixture was cooled then quenched with methanol (30 ml). Water (50 ml) and c.HCl (35 ml) were added and the reaction mixture stirred until all bubbling ceased before concentrating in vacuo. To the residue water (250 ml) was added, before basifying by addition of NH$_4$OH (30 ml). The aqueous layer was extracted with ethyl acetate (3×200 ml) and the combined organic extracts dried over anhydrous magnesium sulphate, filtered and concentrated in vacuo to give the title compound as a white solid (26.1 g, 0.09 mol, 99%). $^1$H NMR (CD$_3$OD, 400 MHz) δ: 0.95 (t, 3H), 1.58 (q, 2H), 2.62 (m, 2H), 2.81 (m, 2H), 4.72 (dd, 1H), 5.05 (s, 2H), 6.95 (d, 2H), 7.24 (m, 3H), 7.35 (t, 2H), 7.41 (d, 2H). LRMS: m/z 286 (M-H$^+$).

EXAMPLE 27

6-(4-benzyloxyphenyl)-4-propylmorpholin-3-one

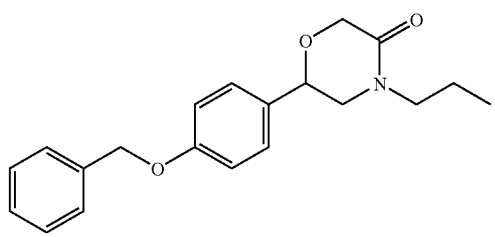

Sodium hydroxide (22.5 g, 0.56 mol) in water (100 ml) was added to the amine from example 26 (26.0 g, 0.09 mol) in dichloromethane (400 ml) and the solution vigorously stirred at room temperature. Chloroacetylchloride (8.6 ml, 0.11 mol) was then added and the reaction mixture stirred for a further 60 minutes. The layers were separated and the aqueous layer re-extracted with dichloromethane (200 ml). The organic extracts were combined, dried over anhydrous magnesium sulphate, filtered and concentrated in vacuo to give a colourless oil. Potassium hydroxide (15.0 g, 0.27 mol), isopropyl alcohol (400 ml) and the colourless oil residue were stirred together as an opaque solution with water (30 ml) for 2 hours. The reaction mixture was concentrated in vacuo and the yellow residue dissolved in ethyl acetate (200 ml). This was partitioned with water (200 ml) then brine (200 ml). The organic fraction was dried over anhydrous magnesium sulphate, filtered and concentrated in vacuo to give the title compound as a white solid (19.9 g, 0.06 mol, 67%). $^1$H NMR (CDCl$_3$, 400 MHz) δ: 0.95 (t 3H), 1.62 (m, 2H), 3.34 (m, 2H), 3.51 (m, 2H), 4.32 (d, 1H), 4.41 (d, 1H), 4.72 (dd, 1H), 5.04 (s, 2H), 6.98 (d, 2H), 7.31-7.43 (m, 7H). LRMS: m/z 326 (M-H$^+$).

EXAMPLE 28

2-(4-benzyloxyphenyl)-4-propylmorpholine

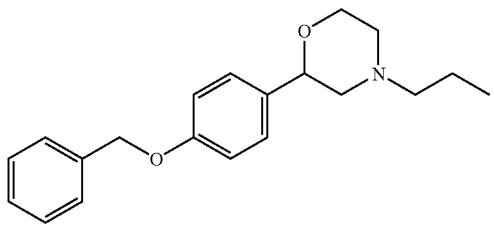

Prepared following the same method as for example 26 with the morpholin-3-one from example 27 (19.9 g, 0.061 mol) to give the title compound as a colourless oil (17 g, 0.055 mol, 90%) $^1$H NMR (CDCl$_3$, 400 MHz) δ: 0.95 (t, 3H), 1.55 (q, 2H), 2.06 (t, 1H), 2.21 (dt, 1H), 2.35 (dd, 2H), 2.80 (d, 1H), 2.91 (d, 1H), 3.82 (dt, 1H), 4.02 (dd, 1H), 4.52 (dd, 1H), 5.05 (s, 2H), 6.98 (t, 2H), 7.24-7.42 (m, 7H). LRMS: m/z 312 (M-H$^+$).

EXAMPLE 29

4-(4-Propylmorpholin-2-yl)phenol

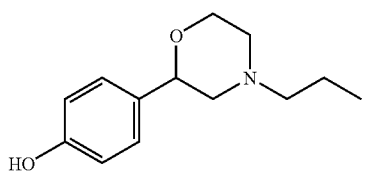

Benzyl ether from example 28 (3.0 g, 9.64 mmol) was dissolved in methanol (150 ml) and 10% palladium on charcoal (800 mg) was added. The reaction mixture was stirred for a few minutes before ammonium formate (6.17 g, 96.4 mmol) was added portionwise. The reaction mixture was carefully heated to 80° C. until gas evolution had ceased. After cooling the reaction mixture was filtered through arbacel, washed with methanol (50 ml) and concentrated in vacuo to give the title compound as a white crystalline solid (1.51 g, 6.83 mmol, 71%). $^1$H NMR (CDCl$_3$, 400 MHz) δ: 0.91 (t, 3H), 1.58 (q, 2H), 2.10 (t, 1H), 2.22 (t 1H), 2.40 (dd, 2H), 2.81 (d, 1H), 2.93 (d, 1H), 3.85 (t, 1H), 4.02 (dd, 1H), 4.57 (d, 1H), 6.79 (d 2H), 7.21 (d 2H). LRMS: m/z 222 (M-H$^+$).

EXAMPLE 30

2-Bromo-4-(4-propylmorpholin-2-yl)phenol

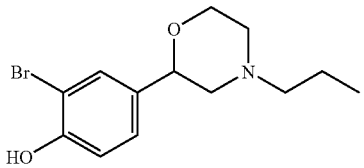

To the phenol from example 29 (200 mg 0.9 mmol) in dichloromethane (5 ml) was added N-bromosuccinimide (161 mg, 0.9 mmol). The reaction mixture was stirred at room temperature for 55 hours, before concentrating in vacuo. The crude product was purified by column chromatography on silica eluting with dichloromethane:methanol (95:5) to give the title compound as a white foam (117.5 mg, 0.39 mmol, 44%). $^1$H NMR (CDCl$_3$, 400 MHz) δ: 0.96 (t, 3H), 1.59 (q, 2H), 2.03 (t, 1H), 2.23 (t, 1H), 2.40 (t, 2H), 2.81 (d, 1H), 2.98 (d, 1H) 3.82 (t, 1H), 4.01 (d, 1H), 4.56 (d, 1H), 6.96 (d, 1H), 7.20 (d, 1H), 7.49 (s, 1H). LRMS: m/z 302 (M-H$^+$, Br isotope).

EXAMPLE 31

2-(4-benzyloxy-3-bromophenyl)-4-propylmorpholine

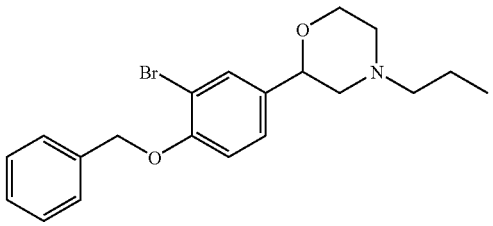

To the phenol from example 30 (117.5 mg, 0.39 mmol) in dry DMF (10 ml), under an atmosphere of nitrogen, was added potassium carbonate (75 mg, 0.54 mmol) and benzyl bromide (0.07 ml, 0.54 mmol). The reaction mixture was heated to 150° C. for 48 hours. After cooing, the reaction mixture was concentrated in vacuo and the residue partitioned between ethyl acetate (50 ml) and water (50 ml). The aqueous layer was then re-extracted with ethyl acetate (2×20 ml). The combined organic extracts were then dried over anhydrous magnesium sulphate, filtered and concentrated in vacuo to give the crude product as a brown oil. This was purified by column chromatography on silica eluting with dichloromethane:methanol (98:2) to give the title compound as a colourless oil (153 mg, 0.39 mmol, 100%). $^1$H NMR (CDCl$_3$, 400 MHz) δ: 0.93 (t, 3H), 1.56 (q, 2H), 2.05 (t, 1H), 2.25 (t, 1H), 2.37 (t, 2H), 2.82 (d, 1H), 2.92 (d, 1H), 3.85 (t, 1H), 4.02 (d, 1H), 4.52 (d, 1H), 5.15 (s, 2H), 6.87 (d, 1H), 7.20 (d, 1H), 7.30 (d, 1H), 7.37 (t, 2H), 7.45 (d, 2H), 7.58 (s, 1H). LRMS: m/z 392 (M-H$^+$).

EXAMPLE 32

2-Benzyloxy-5-(4-propylmorpholin-2-yl)benzoic acid methyl ester

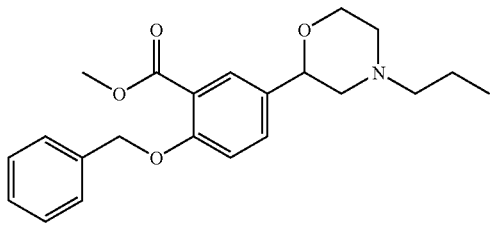

To the bromide from example 31 (153 mg, 0.39 mmol) in dry DMF (4 ml) was added triethylamine (2.1 ml, 0.78 mmol) and methanol (2 ml) and the reaction mixture stirred for 5 minutes. [1,1'-Bis(diphenylphosphino)ferrocene]dichloropalladium (II), complex with dichloromethane (1:1) (16 mg, 0.02 mmol) was added before carbon monoxide (g) (3 inflated balloons) was bubbled through the reaction mixture. The reaction mixture was then heated to 100° C. for 16 hours under an atmosphere of carbon monoxide. After cooling, the reaction mixture was concentrated in vacuo and the residue partitioned between ethyl acetate (25 ml) and water (20 ml). The organic layer was separated, washed with brine (20 ml) and dried over anhydrous magnesium sulphate, filtered and concentrated in vacuo to give a black solid. Purification by column chromatography on silica eluting with dichloromethane:methanol:ammonia (90:10:1) gave the title compound as a colourless oil (105 mg, 0.28 mmol, 73%). $^1$H NMR (CDCl$_3$, 400 MHz) δ: 0.94 (t, 3H), 1.60 (m, 2H), 2.18 (s, 4H), 2.43 (m, 2H), 3.00 (m, 2H), 3.90 (s, 3H), 4.04 d, 1H), 5.18 (s, 2H), 5.97 (d, 1H), 7.26-7.47 (m, 6H), 7.82 (s, 1H). LRMS: m/z 370 (M-H$^+$).

EXAMPLE 33

2-Benzyloxy-5-(4-propylmorpholin-2-yl)benzoic acid

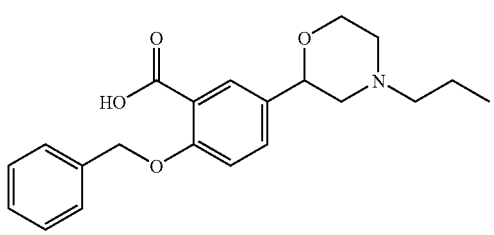

To the methyl ester from example 32 (105 mg, 0.28 mmol) in methanol (5 ml) was added 10% sodium hydroxide (aq) (15 ml) and the milky white suspension was refluxed for 2 hours. The now colourless reaction mixture was cooled then neutralised by addition of 2M HCl (aq) (few drops). The reaction mixture was then concentrated in vacuo to give the title compound as an off-white solid (99 mg, 0.28 mmol, 100%). LRMS: m/z 355 (M-H$^+$). This material was taken on crude to example 34.

EXAMPLE 34

2-Benzyloxy-5-(4-propylmorpholin-2-yl benzamide

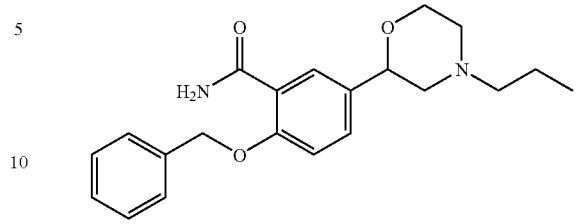

To the crude benzoic acid from example 33 (99 mg, 0.28 mmol) was added thionyl chloride (5 ml) and the reaction mixture heated to 50° C. for 2 hours. The reaction mixture was cooled and the excess thionyl chloride was removed in vacuo. The residue was then dissolved in dichloromethane (10 ml) and ammonia (g) was bubbled through the reaction mixture for 10 minutes. The resulting suspension was stirred at room temperature for 1 hour before concentrating in vacuo. The crude material was purified by column chromatography on silica eluting with dichloromethane:methanol:ammonia (95:5:0.5) to give the title compound as an off-white solid (88 mg, 0.25 mmol, 90%). $^1$H NMR (CDCl$_3$, 400 MHz) δ: 0.94 (t, 3H), 1.59 (n, 2H), 2.15-2.42 (m, 4H), 2.87 (m, 1H), 3.03 (m, 1H), 3.96 (m, 1H), 4.02 (d, 1H), 4.67 (m, 1H), 5.19 (s, 2H), 5.72 (m, 1H), 7.04 (d, 1H), 7.41 (m, 5H), 7.50 (d, 1H), 7.70 (m, 1H), 8.21 (s, 1H). LRMS: m/z 355 (M-H$^+$),

EXAMPLE 35

2-Hydroxy-5-(4-propylmorpholin-2-yl)benzamide

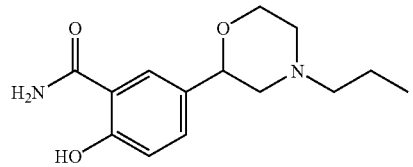

Prepared using the same method as for example 29 with the benzyl ester from example 34 (80 mg, 0.22 mmol) to give the title compound as an off-white solid (56 mg, 0.21 mmol, 96%). $^1$H NMR (CDCl$_3$, 400 MHz) δ: 0.95 (t, 3H), 1.55 (m, 2H), 2.13 (t, 1H), 2.29 (t, 1H), 2.42 (m, 2H), 2.88 (d, 1H), 2.97 (d, 1H), 3.81 (t, 1H), 4.00 (d, 1H), 4.49 (d, 1H), 6.87 (d, 1H), 7.42 (d, 1H), 7.78 (s, 1H). LRMS: m/z 265 (M-H$^+$).

EXAMPLE 36

2-Nitro-4-(4-propylmorpholin-2-yl)phenol

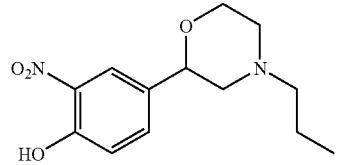

The phenol from example 29 (100 mg, 0.45 mmol) was dissolved in nitric acid:water (1:3) (2 ml) and stirred at room temperature for 10 minutes. The reaction mixture was then diluted with water (5 ml) and basified with NH$_4$OH (1 ml), before extracting into ethyl acetate (3×10 ml). The organic extracts were combined and dried over anhydrous magnesium sulphate, filtered and concentrated in vacuo to give the title compound as a yellow solid (95 mg, 0.35 mmol, 79%). $^1$H NMR (CDCl$_3$, 400 MHz) δ: 0.97 (t, 3H), 1.33 (t, 2H), 1.43-1.79 (bm, 4H), 2.02 (d, 3H), 4.06 (m, 2H), 7.17 (d, 1H), 7.60 (d, 1H), 8.16 (s, 1H), 10.55 (bs, 1H). LRMS: m/z 267 (M-H⁻).

EXAMPLE 37

2-Amino-4-(4-propylmorpholin-2-yl)phenol

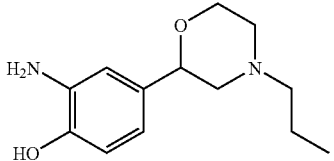

To the nitro from example 36 (95 mg, 0.35 mmol) in ethanol (10 ml) was added 10% palladium on charcoal (50 mg) and ammonium formate (100 mg, XS). The reaction mixture was gently heated to 70° C. and held at this temperature for 1 hour before it was allowed to cool to room temperature.

The reaction mixture was then filtered through arbacel and washed with ethanol (20 ml) then dichloromethane (20 ml). The organic washes were combined and concentrated in vacuo to give the title compound as a yellow solid (65 mg, 0.28 mmol, 78%). ¹H NMR (CDCl₃, 400 MHz) δ: 0.91 (t, 3H), 1.55 (m, 2H), 2.12 (t, 1H), 2.25 (dt, 1H), 2.40 (t, 2H), 2.81-2.92 (dd, 2H), 3.82 (t, 1H), 4.00 (d, 1H), 4.42 (d, 1H), 6.60 (m, 2H), 6.71 (s, 1H). LRMS: m/z 237 (M-H⁺),

EXAMPLE 38

5-Bromo-2-(2,5-dimethylpyrrol-1-yl pyridine

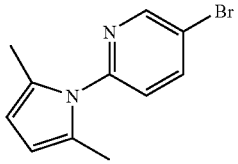

5-Bromopyridin-2-yl-amine (13.8 g, 0.08 mol), acetonylacetone (14.1 ml, 0.12 mol) and p-toluenesulphonic acid (100 mg) were dissolved in toluene (180 ml) and refluxed under Dean Stark conditions for 14 hours. After cooling, the brown solution was poured into water (200 ml) and extracted with toluene (2×200 ml). The organic extracts were combined and washed with brine (50 ml) then dried over anhydrous magnesium sulphate, filtered and concentrated in vacuo to give crude product. This was purified by column chromatography on silica eluting with ethyl acetate:pentane (1:3) to give the title compound as a brown oil (18.4 g, 0.073 mol, 92%). ¹H NMR (CDCl₃, 400 MHz) δ: 2.18 (s, 6H), 5.90 (s, 2H), 7.11 (d, 1H), 7.92 (d, 1H), 8.62 (s, 1H). LRMS: m/z 253 (M-H⁺, Br isotope).

EXAMPLE 39

2-Chloro-1-[6-(2,5-dimethylpyrrol-1-yl)pyridin-3-yl] ethanone

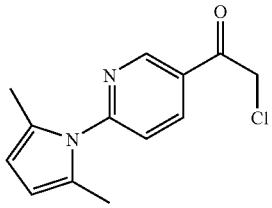

To a solution of bromo pyridine from example 38 (2 g, 8.0 mmol) at –78° C. in dry THF (30 ml), was added butyllithium (2.5M in hexanes) (3.5 ml 8.8 mmol), dropwise over 20 minutes. The reaction mixture was stirred for 30 minutes then 2-chloro-N-methoxy-N-methylacetamide (1.2 g, 8.8 mmol) in dry THF (20 ml) was added dropwise keeping the temperature at –78° C. Stirring was continued for 30 minutes at this temperature before 1M HCl (aq) (50 ml) was added and the reaction mixture warmed to room temperature. The organic layer was separated and the aqueous layer washed with ethyl acetate (50 ml). The organic layers were combined then washed with 3M NaOH (aq) (10 ml) and brine (10 ml) before being dried over an hydrous magnesium sulphate, filtered and concentrated in vacuo to give crude title compound as a brown oil (1.34 g, 5.4 mmol, 67%). ¹H NMR (CDCl₃, 400 MHz) δ: 2.20 (s, 6H), 4.68 (s, 2H), 5.92 (s, 2H), 7.32 (d, 1H), 8.38 (d, 1H), 9.16 (s, 1H). LRMS: m/z 249 (M-H⁺).

EXAMPLE 40

2-(2,5-dimethylpyrrol-1-yl)-5-oxiranylpyridine

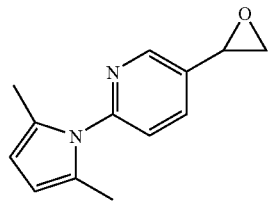

To the ketone from example 39 (1.34 g, 5.4 mmol) dissolved in dry THF (20 ml), cooled to 0° C., was added sodium borohydride (308 mg, 8.1 mmol) portionwise. The reaction mixture was stirred for 2 hours then 3M NaOH (aq) (10 ml) was added and stirring continued for a further 16 hours. The reaction mixture was extracted with ethyl acetate (2×29 ml) and the combined organic extracts washed with brine (5 ml), dried over anhydrous magnesium sulphate, filtered and concentrated in vacuo. The residue was purified by column chromatography on silica eluting with ethyl acetate:pentane (1:5) to give the title compound as a colourless oil (900 mg, 4.2 mmol, 78%). ¹H NMR (CDCl₃, 400 MHz) δ: 2.13 (s, 6H), 2.91 (dd, 1H), 3.25 (t, 1H), 3.98 (t, 1H), 5.90 (s, 2H), 7.20 (d, 1H), 7.62 (dd, 1H), 8.58 (s, 1H). LRMS: m/z 215 (M-H⁺).

EXAMPLE 41

1-[6-(2,5-dimethylpyrrol-1-yl)pyridin-3-yl]-2-propylaminoethanol

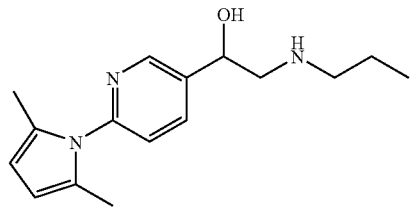

To the epoxide from example 40 (900 mg, 4.2 mmol) in DMSO (5 ml) was added propylamine (4 ml, 4.8 mmol) and the reaction mixture was heated to 40° C. for 4 days. The reaction mixture was then cooled and 3M HCl (aq) (10 ml) and water (10 ml) were added before washing with diethyl ether (2×10 ml). This organic layer was discarded. The aqueous layer was basified with NH₄OH (5 ml) and extracted with ethyl acetate (3×10 ml). The organic extracts were combined and dried over anhydrous magnesium sulphate, filtered and concentrated in vacuo to give the title compound as an oil (1.15 g, 4.2 mmol, 100%). ¹H NMR (CDCl₃, 400 MHz) δ: 0.93 (t, 3H), 1.62 (m, 2H), 2.11 (s, 6H), 2.69-2.82 (m, 3H), 3.06 (dd, 1H), 3.60 (bs, 2H), 4.92 (dd, 1H), 5.84 (s, 2H), 7.20 (d, 1H), 7.88 (d, 1H), 8.61 (s, 1H). LRMS: m/z 274 (M-H⁺).

EXAMPLE 42

6-[6-(2,5-dimethylpyrrol-1-yl)pyridin-3-yl]-4-propylmorpholi-3-one

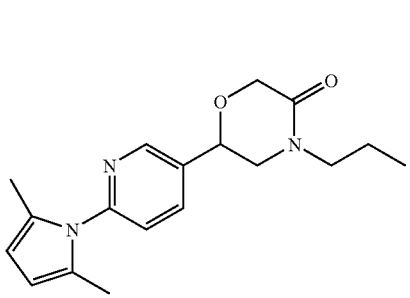

Prepared following the same method as for example 27 with the amine from example 41 (1.15 g, 4.2 mmol). Purification by column chromatography on silica eluting with dichloromethane-, methanol (98.2) gave the title compound as a brown film (191 mg, 0.61 mmol, 14%). $^1$H N MR (CDCl$_3$, 400 MHz) δ: 0.97 (t, 3H), 1.65 (m, 2H), 2.13 (s, 6H), 3.38 (m, 1H), 3.42-3.56 (m, 2H), 6.61 (t, 1H), 4.35 (d, 1H), 4.45 (d, 1H), 4.91 (dd, 1H), 6.91 (s, 2H), 7.22 (d, 1H), 7.89 (d, 1H), 8.61 (s, 1H). LRMS: m/z 314 (M-H$^+$).

EXAMPLE 43

6-[6-(2,5-dimethylpyrrol-1-yl)pyridin-3-yl]-4-propylmorpholine

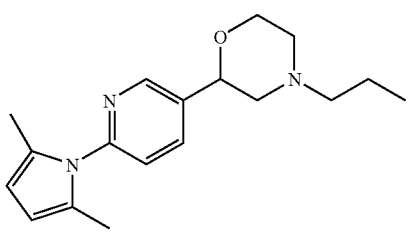

To a solution of the morpholin-3-one from example 42 (191 mg, 0.61 mmol) in dry THF (5 ml) was added lithium aluminium hydride (1M solution in diethyl ether) (1.25 ml, 0.61 mmol) and the reaction mixture was warmed to reflux for 2.5 hours. The reaction mixture was cooled to room temperature then 1M NaOH (1.25 ml) was added to give a white precipitate. The reaction mixture was filtered and concentrated in vacuo. The white solid was discarded. The concentrated filtrate was purified by column chromatography on silica eluting with dichloromethane:methanol (95:5) to give the title compound as a white film (108 mg, 0.36 mmol, 59%). $^1$H NMR (CDCl$_3$, 400 MHz) δ: 0.92 (t, 3H), 1.61 (q, 2H), 2.10 (s, 6H), 2.15 (m, 1H), 2.29 (dt, 1H), 2.40 (t, 2H), 2.82 (d, 1H), 3.02 (d, 1H), 3.90 (t, 1H), 4.08 (d, 1H), 4.71 (d, 1H), 5.89 (s, 2H), 7.20 (d, 1H), 7.81 (d, 1H), 8.60 (s, 1H). LRMS: m/z 300 (M-H$^+$).

EXAMPLES 44A AND 44B 5-(4-propylmorpholin-2-yl)pyridin-2-ylamine

To the 2,5-dimethylpyrrole from example 43 (45 mg, 0.15 mmol) in ethanol (3 ml) was added hydroxylamine hydrochloride (52 mg, 0.75 mmol) and the reaction mixture heated to 80° C. for 20 hours. The reaction mixture was cooled to room temperature and concentrated in vacuo. The residue was purified by column chromatography on silica eluting with dichloromethane: methanol:ammonia (90:10:1) to give the racemic compound as a colourless film (31 mg, 0.14 mmol, 94%). $^1$H NMR (CDCl$_3$, 400 MHz) δ: 0.92 (t, 3H), 1.60 (m, 2H), 2.11 (t, 1H), 2.25 (dt, 1H), 2.41 (t, 2H), 2.82-2.91 (dd, 2H), 3.89 (dt, 1H), 4.01 (dd, 1H), 4.57 (bd, 3H), 6.49 (d, 1H), 7.42 (d, 1H), 8.02 (s, 1H). LRMS: m/z 222 (M-H$^+$).

A sample of this racemic product (580 mg) was separated into it's consituent enantiomers by chiral HPLC Conditions used: Chiralpak AD column (250×21.2 mm), Eluent methanol:ethanol (1:1), flow rate 15 mL/min.

The faster eluting enantiomer Example 44A (retention time 8.3 min) was obtained in >99% ee $^1$H NMR (CDCl$_3$, 400 MHz) was identical to that of the racemate. LRMS: m/z 222. Analysis found C, 63.54; H, 8.60; N, 18.38%. C$_{12}$H$_{19}$N$_3$O.3H$_2$O requires C, 63.58; H, 8.71; N, 18.53%. $[\alpha]_{546}^{25}$ −2.1(c=0.12, MeOH); $[\alpha]_{436}^{25}$ −8.9(c=0.12, MeOH)

The slower eluting enantiomer Example 44B (retention time 9.4 min) was obtained in 98.9% e.e.

$^1$H NMR (CDCl$_3$, 400 Hz) was identical to that of the racemate. LRMS: m/z 222. Analysis found C, 63.53; H, 8.57; N, 18.36%. C$_{12}$H$_{19}$N$_3$O.3H$_2$O requires C, 63.58; H, 8.71; N, 18.53%. $[\alpha]_{546}^{25}$ +2.4(c=0.12, MeOH); $[\alpha]_{436}^{25}$ +7.2(c=0.12, MeOH)

EXAMPLE 45

2-Ethyl-6-(3-methoxy-phenyl)-4-propyl-morpholin-3-one

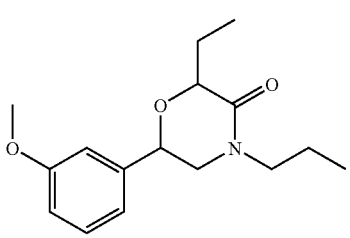

Sodium hydroxide (0.48 g, 12.0 mmol) in water (2 mL) was added to the product from example 3 (0.50 g, 2.4 mmol) in dichloromethane (5 mL) and the mixture stirred at room temperature. 2-Chlorobutyryl chloride (0.28 mL, 2.87 mmol) was then added dropwise and the reaction mixture stirred for 60 hours. The reaction mixture was diluted with dichloromethane (10 mL) and the aqueous layer was separated. The organic layer was dried over anhydrous magnesium sulphate, filtered and concentrated in vacuo to give the crude product as a clear oil (contained mixture of cyclised and uncyclised material) (0.57 g). LRMS: m/z 314 (M-H+ of uncyclised material), 296 (M-H+ less water), 278 (M-H+ of cyclised product). Potassium hydroxide (0.13 g, 2.20 mmol) was dissolved in water (1 mL) and added to a solution of the crude product (0.57 g, 1.83 mmol) in isopropyl alcohol (5 mL). The reaction mixture was stirred at room temperature overnight and the organic solvent then evaporated in vacuo. The residue was dissolved in ethyl actetate (10 mL) and the aqueous layer separated. The organic layer was dried over anhydrous magnesium sulphate, filtered and concentrated in vacuo to give the crude product as an oil. The residue was purified by column chromatography on silica eluting with ethyl acetate: pentane (1:5 to 1:1) to give the title compound as a clear oil (326 mg, 1.17 mmol, 49%) as a mixture of diastereomers. $^1$H NMR (CDCl$_3$, 400 MHz) δ: 0.90 (t, 3H), 1.00 (t, 3H), 1.60 (m, 2H), 2.00 (bm, 2H), 3.10-3.60 (m, 4H), 3.80 (s, 3H), 4.20 (d, 0.5H), 4.25 (d, 0.5H), 4.75 (d, 0.5H), 4.90 (d, 0.5H), 6.80 (d, 1H), 6.90 (m, 2H), 7.25 (m, 1H). LRMS (APCI): m/z 278 (MH+), 276 (MH−).

EXAMPLES 46A AND 46B

2-Ethyl-6-(3-methoxy-phenyl)-4-propyl-morpholine

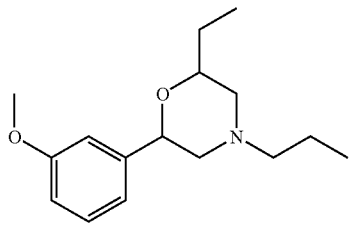

Borane-tetrahydrofuran complex (1M in THF) (3 mL, 3 mmol) was added dropwise to the product from example 45 (0.33 g, 1.18 mmol) in dry THF (4 mL) under an atmosphere of nitrogen. The reaction mixture was heated at 85° C. for 3 hours then cooled and quenched by the addition of methanol (1 mL). The reaction mixture was then concentrated in vacuo and the residue suspended in 6N HCl (aq) (10 mL) and heated to 60° C. for 1.5 hours. The reaction mixture was cooled and extracted with diethyl ether (2×10 mL). The aqueous layer was rendered basic (pH 9-10) by addition of solid potassium carbonate before re-extracting with dichloromethane (2×15 mL). The dichloromethane extracts were dried over anhydrous magnesium sulphate, filtered and concentrated in vacuo to give the crude products as a clear oil. Purification by column chromatography on silica eluting with ethyl acetate, pentane (1:10) yielded the two title compounds as single diastereomers.

Example 46A: clear oil (0.10 g, 0.3 mmol, 32%): $^1$H NMR (CDCl$_3$, 400 MHz) δ: 1.00 (m 6H), 1.60 (bm, 3H), 1.85 (m, 1H), 2.25 (bt, 2H), 2.35 (s, 1H), 2.45 (m, 1H), 2.60 (m, 1H), 2.65 (m, 1H), 3.70 (s, 1H), 3.80 (s, 3H), 4.80 (s, 1H), 6.80 (d, 1H), 7.00 (m, 2H), 7.25 (m, 1H). LRMS (APCI): m/z 264 (M-H+).

Example 46B: clear oil (0.10 g, 0.38 mmol, 32%): $^1$H NMR (CDCl$_3$, 400 MHz) δ: 0.90 (t, 3H), 1.00 (t, 3H), 1.60 (bm, 4H), 1.80 (bs, 1H), 2.00 (bs, 1H), 2.35 (bs, 2H), 2.85 (bd, 1H), 2.95 (bd, 1H), 3.60 (s, 1H), 3.80 (s, 3H), 4.60 (s, 1H), 6.80 (d, 1H), 6.95 (s, 2H), 7.25 (t, 1H). LRMS (APCI): m/z 264 (MH+).

EXAMPLE 47A 3-(6-Ethyl-4-propyl-morpholin-2-yl)-phenol

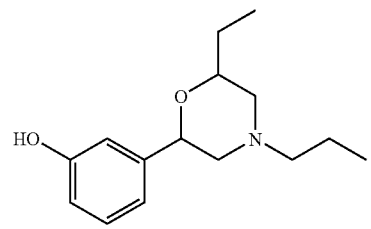

Hydrobromic acid (48% aq., 5 mL) and the product from example 46A (0.10 g, 0.38 mmol) were heated at 80° C. for 16 hours. After cooling the reaction mixture was concentrated in vacuo. The residue was partitioned between aqueous ammonia (0.880, 15 mL) and dichloromethane (15 mL), the layers were separated and the aqueous layer re-extracted with dichloromethane (2×15 mL). The organic extracts were combined, dried over anhydrous magnesium sulphate, filtered and concentrated in vacuo. The crude product was purified by column chromatography on silica eluting with dichloromethane, then dichloromethane:methanol (99:1 to 95:5) to yield the title compound as a clear oil (65 mg 0.26 mmol, 69%) as the single diastereoisomer. $^1$H NMR (CDCl$_3$, 400 MHz) δ: 0.95 (m 6H), 1.60 (m, 3H), 1.85 (m, 1H), 2.25 (m, 2H), 2.45 (m, 2H), 2.55 (q, 1H), 2.75 (d, 1H), 3.75 (s, 1H), 4.80 (m, 1H), 6.70 (d, 1H), 6.90 (s, 1H), 7.00 (1H, d), 7.25 (t, 1H). LRMS (APCI): m/z 250 (MH+). Analysis found C, 70.94%; H, 9.16%; N, 5.53%. C$_{15}$H$_{23}$NO$_2$.0.3H$_2$O requires C, 70.72%; H, 9.34%; N, 5.50%.

EXAMPLE 47B 3-(6-Ethyl-4-propyl-morpholin-2-yl)-phenol

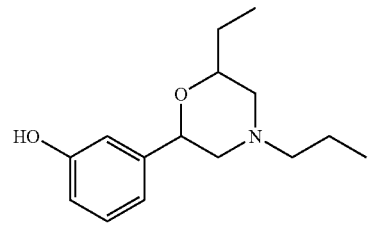

Prepared following the same method as for example 47A with the product from example 46B (0.10 g, 0.38 mmol). Purification by column chromatography on silica was not required. The title compound was obtained as a yellow oil (57 mg, 0.23 mmol, 60%) as the single diastereoisomer. $^1$H NMR (CDCl$_3$, 400 Hz) δ: 0.90 (t, 3H), 1.00 (t, 3H), 1.60 (m, 4H), 1.85 (t, 1H), 2.00 (t, 1H), 2.35 (m, 2H), 2.90 (d, 1H), 3.00 (d, 1H), 3.65 (m, 1H), 4.60 (m, 1H), 6.75 (d, 1H), 6.80 (s, 1H), 6.90 (1H, d), 7.20 (t 1H). LRMS (ESI): m/z 250 (MH+), 248 (M-H−). Analysis found C, 71.63%; H, 9.19%; N, 5.55%. C$_{15}$H$_{23}$NO$_2$.0.1H$_2$O requires C, 71.73%, H, 9.31%; N, 5.58%.

EXAMPLE 48

2-Methyl-6-(3-methoxy-phenyl)-4-propyl-morpholin-3-one

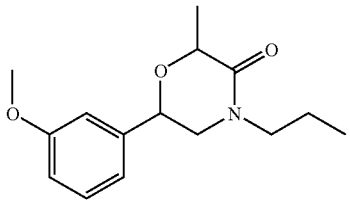

Prepared following the same method as for example 45 with the product from example 3 (0.44 g, 2.10 mmol) and 2-chloropropionyl chloride (0.25 mL, 2.50 mmol). Purification by column chromatography on silica of the title compound was not required. The title compound was obtained as a clear oil (0.42 g, 1.60 mmol, 76%) as a mixture of diastereomers. $^1$H NMR (CDCl$_3$, 400 MHz) δ: 0.95 (t, 3H), 1.60 (m, 5H), 3.30 (bm, 2H), 3.50 (bm, 2H), 3.80 (s, 3H), 4.40 (q, 0.5H), 4.55 (q, 0.5H), 4.80 (dd, 0.5H), 4.95 (dd, 0.5H), 6.85 (d, 1H), 6.95 (s, 2H), 7.25 (m, 1H). LRMS (APCI): m/z 264 (MH$^+$), 262 (MH$^-$).

EXAMPLE 49A AND 49B

2-Methyl-6-(3-methoxy-phenyl)-4-propyl-morpholine

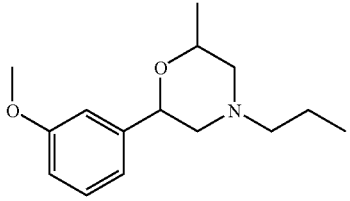

Prepared following the same method as for example 46 with the product from example 48 (0.42 g, 1.6 mmol). Purification by column chromatography on silica eluting with ethyl acetate:pentane (1:6) yielded the two title compounds as single diastereomers.

Example 49A: clear oil (0.10 g, 0.40 mmol, 25%): $^1$H NMR (CDCl$_3$, 400 MHz) δ: 0.95 (t 3H), 1.30 (d, 3H), 1.60 (m, 2H), 2.20-2.35 (m, 3H), 2.50 (d, 1H), 2.60 (m, 1H), 2.65 (d, 1H), 3.80 (s, 3H), 4.00 (s, 1H), 4.85 (s, 1H), 6.80 (d, 1H), 7.05 (m, 2H), 7.25 (m, 1H). LRMS (APCI): m/z 250 (MH$^+$).

Example 49B: clear oil (0.10 g, 0.40 mmol, 25%): $^1$H NMR (CDCl$_3$, 400 MHz) δ: 0.90 (t 3H), 1.25 (m, 3H), 1.60 (m, 2H), 1.80 (m, 1H), 2.00 (bm, 1H), 2.35 (s, 2H), 2.80 (d, 1H), 2.90 (d, 1H), 3.80 (s, 3H), 3.85 (s, 1H), 4.60 (sa 1H), 6.80 (d, 1H), 7.00 (m, 2H), 7.25 (m, 1H). LRMS (APCI): m/z 250 (MH$^+$).

EXAMPLE 50A 3-(6-Methyl-4-propyl-morpholin-2-yl)-phenol

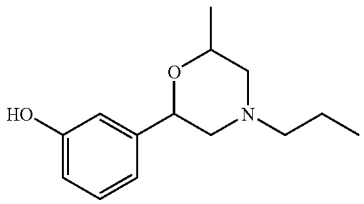

Prepared following the same method as for example 47A with the product from example 49A (0.10 g, 0.4 mmol). Purification by column chromatography on silica eluting with dichloromethane, then dichloromethane:methanol (99:1) yielded the title compound as a clear oil (70 mg, 0,30 mmol, 74%) as the single diastereoisomer. $^1$H NMR (CDCl$_3$, 400 MHz) δ: 0.95 (t, 3H), 1.35 (d, 3H), 1.55 (m, 2H), 2.25 (m, 2H), 2.35 (m, 1H), 250 (m, 1H), 2.55 (m, 1H), 2.75 (d, 1H), 4.05 (s, 1H), 4.85 (m, 1H), 6.70 (d, 1H), 6.90 (s, 1H), 7.00 (1H, d), 7.20 (t, 1H). LRMS (APCI): m/z 236 (MH$^+$). Analysis found C, 70.62%; H, 8.89%; N, 5.95%. O$_{14}$H$_{21}$NO$_2$.0.1H$_2$O requires C, 70.91%; H, 9.01%; N, 5.91%.

EXAMPLE 50B 3-(6-Methyl-4-propyl-morpholin-2-yl)-phenol

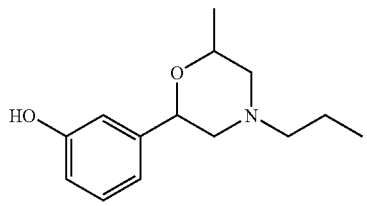

Prepared following the same method as for example 47A with the product from example 49B (0.10 g, 0.4 mmol). Purification by column chromatography on silica was not required. The title compound was obtained as a yellow oil (100 mg, 0.42 mmol, 103%—contained 3% starting material) as the single diastereomer. $^1$H NMR (CDCl$_3$, 400 Hz) δ: 0.90 (t, 3H), 1.25 (d, 3H), 1.60 (m, 2H), 1.85 (m, 1H), 2.00 (m, 1H), 2.35 (m, 2H), 2.85 (d, 1H), 3.00 (d, 1H), 3.85 (s 1H), 4.60 (d 1H), 6.75 (d, 1H), 6.80 (s, 1H), 6.90 (1H, d), 7.20 (m, 1H). LRMS (APCI): m/z 236 (MH$^+$). Analysis found C, 69.38%; H, 8.86%; N, 5.73%. C$_{14}$H$_{21}$NO$_2$.0.45H$_2$O requires C, 69.33%; H, 9.06%; N, 5.78%.

EXAMPLE 51

1-(4-Chloro-3-methoxy-phenyl)-2-propylamino-ethanol

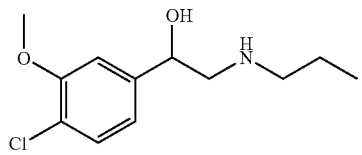

Sodium triacetoxyborohydride (1.25 g, 5.89 mmol) was added with care to a solution of 2-amino-1-(4-chloro-3-methoxy-phenyl)-ethanol (J. Med. Chem., 30(10), 1887, (1987)) (600 mg, 2,98 mmol) and propionaldehyde (0.22 mL, 2.96 mmol) in dichloromethane (10 mL), and the reaction mixture was stirred at room temperature for 1 hour. Sodium bicarbonate solution (sat. aq., 10 mL) was added dropwise and then the reaction mixture was diluted further with water (20 mL) and dichloromethane (20 mL). The aqueous layer was separated and re-extracted with dichloromethane (2×20 mL). The combined organic layers were dried over anhydrous magnesium sulphate, filtered and concentrated in vacuo. The crude product was purified by column chromatography on silica eluting with dichloromethane:methanol:0.880 ammonia (95:5:0.5 to 92:8:0.8) to yield the title compound as a solid (320 mg, 1.31 mmol, 44%). $^1$H NMR (CDCl$_3$, 400 MHz) δ: 0.90 (t, 3H), 1.50 (q, 2H), 2.50-2.70 (m, 5H), 2.90 (dd, 1H), 3.80 (s, 3H), 4.65 (dd, 1H), 6.85 (d, 1H), 7.00 (1H, d), 7.30 (bd, 1H). LRMS (APCI): m/z 244 (MH$^+$), 226 (MH$^+$ less H$_2$O).

EXAMPLE 52

6-(4-Chloro-3-methoxy-phenyl)-4-propyl-morpholin-3-one

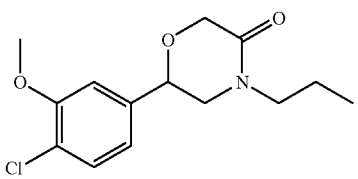

Chloroacetyl chloride (0.11 mL, 1.33 mmol) was added to a solution of the product from example 51 (0.31 g, 1.27 mmol) and triethylamine (0.19 mL, 1.36 mmol in dichloromethane (10 mL) and stirred at room temperature for 60 hours. The reaction mixture was diluted with dichloromethane (20 mL) and washed with hydrochloric acid (aq. 1N: 10 mL), water (10 mL) and sodium bicarbonate solution (sat. aq., 10 mL). The organic layer was dried over anhydrous magnesium sulphate, filtered and concentrated in vacuo to yield the uncyclised product as an oil (0.40 g). LRMS (APCI): m/z 320 (MH$^+$ of uncyclised product), 302 (MH$^+$ less water), 284 (MH$^+$ of cyclised product). Potassium hydroxide (0.75 g 1.33 mmol) was added to a solution of the uncyclised product (0.40 g, 1.23 mmol) in isopropyl alcohol (10 mL) and water (0.4 mL) and stirred at room temperature for 16 hours. The reaction mixture was concentrated in vacuo and partitioned between dichloromethane (30 mL) and water (30 mL). The layers were separated and the aqueous layer re-extracted with dichloromethane (2×20 mL). The combined organics were washed with water (30 mL), dried over anhydrous magnesium sulphate, filtered and concentrated in vacuo to yield the title compound as an oil (0.34 g, 1.19 mmol, 94%). $^1$H NMR (CDCl$_3$, 400 MHz) δ: 0.95 (t, 3H), 1.60-1.70 (m, 2H), 3.30-3.40 (m, 2H), 3.40-3.55 (m, 2H), 3.95 (s, 3H), 4.35 (bd, 1H), 4.42 (bd, 1H), 4.78 (dd, 1H), 6.85 (dd, 1H), 7.00 (s, 1H), 7.38 (dd, 1H). LRMS (APCI): m/z 284 (MH$^+$).

EXAMPLE 53

6-(4-Chloro-3-methoxy-phenyl)-4-propyl-morpholine

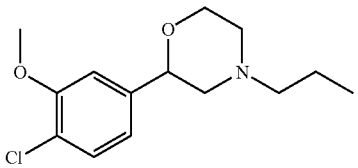

Borane-tetrahydrofuran complex (1M in THF) (3.5 mL, 3.5 mmol) was added dropwise to a solution of the product from example 52 (0.33 g 1.16 mmol) in dry THF (3 mL) under an atmosphere of nitrogen. The reaction mixture was refluxed for 2.5 hours then cooled and quenched by addition of methanol (1 mL). The reaction mixture was concentrated in vacuo and the residue suspended in 4N HCl (aq., 8 mL) and refluxed for 2 hours. The reaction mixture was cooled and extracted with dichloromethane (2×10 mL). The organic layers were discarded. The aqueous layer was rendered basic (pH 9-10) by addition of solid potassium carbonate before re-extracting with dichloromethane (2×15 mL). The dichloromethane extracts were washed with water (10 mL), dried over anhydrous magnesium sulphate, filtered and concentrated in vacuo to give the title compound as an oil (0.31 g: 1.15 mmol, 99%). $^1$H NMR (CDCl$_3$, 400 MHz) δ: 0.95 (t, 3H), 1.45-1.60 (m, 2H), 2.00 (t, 1H), 2.20 (t, 1H), 2.35 (t, 2H), 2.80 (d, 1H), 2.90 (d, 1H), 3.80 (t, 1H), 3.90 (s, 3H), 4.03 (dd 1H), 4.55 (d 1H), 6.85 (dd 1H), 7.00 (s, 1H), 7.30 (dd, 1H). LRMS (APCI): m/z 270 (MH$^+$).

EXAMPLE 54

2-Chloro-5-(4-propyl-morphlin-2-yl)-phenol

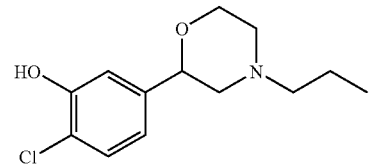

Prepared following the same method as for example 7b (although refluxing was continued for 2.5 hours rather than 1 hour) with the product from example 53 (0.28 g, 1.02 mmol). Purification by column chromatography on silica was not required. The title compound was yielded as a pale brown gum (0.21 g, 0.82 mmol, 81%). $^1$H NMR (CDCl$_3$, 400 MHz) δ: 0.93 (t, 3H), 1.55 (q, 2H), 2.0 (t, 1H), 2.20 (dt, 1H), 2.30-2.40 (m, 2H), 2.80 (bd, 1H), 2.90 (bd, 1H), 3.80 (dt, 1H), 4.0 (dd, 1H), 4.30 (d, 1H), 6.87 (dt, 1H), 7.02 (fd, 1H), 7.25 (s, 1H). LRMS (APCI): m/z 256 (MH$^+$). Analysis found C, 60.71%; H, 7.10%; N, 5.45%. C$_{13}$H$_{18}$NO$_2$Cl requires C, 61.05%; H, 7.09%; N, 5.48%.

EXAMPLE 55

Methyl(2S)-2-(propionylamino)propanoate

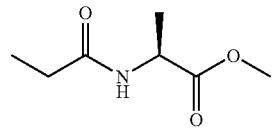

L-Alanine methyl ester hydrochloride salt (14 g, 0.1 mol) was dissolved in dichloromethane (150 mL) and treated with triethylamine (30.45 g, 0.3 mmol). The solution was stirred and propionyl chloride added dropwise. After stirring overnight the mixture was quenched by addition of 1M hydrochloric acid (200 mL) and the organic layer separated. The aqueous layer was re-extracted with dichloromethane (3×200 mL) and the combined organic layers were dried with magnesium sulfate, filtered and evaporated to a to a clear oil (16.0 g, quant.).

$^1$H NMR (DMSO-d6, 400 MHz) δ: 0.95 (t, 3H), 1.25 (d, 3H), 2.1 (q, 2H), 3.6 (s, 3H), 4.2 (quin, 1H), 8.2 (bd, 1H). LRMS (ESI+) m/z 160 (MH$^+$)

EXAMPLE 56 tert-butyl(1S)-2-hydroxy-1-methylethyl-(propyl) carbamate

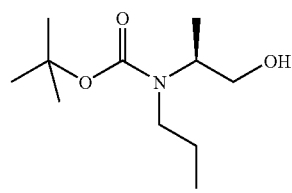

The product from example 55 was dissolved in tetrahydrofuran (200 mL) and borane-tetrahydrofuran complex (300 mL, 0.3 mol) was added to the stirred solution at room temperature. The mixture was then heated at reflux overnight. After cooling to room temperature, the reaction was quenched by the cautious addition of 6M hydrochloric acid (100 mL) and then heated to reflux for 6 hours. The reaction mixture was allowed to cool to room temperature overnight, and then evaporated to dryness (11.77 g). The crude mixture gave m/z 118 consistent with the desired aminoalcohol intermediate. The crude mixture was then dissolved in methanol (50 mL) and water (400 mL) before the addition of potassium hydroxide (28.22 g, 0.5 mol). Di-tert-butyl dicarbonate (32.87 g 0.15 mol) was added to the mixture and stirring continued over 3 days. The reaction mixture was partitioned between DCM (500 mL) and water (100 mL), the organic layer separated and the aqueous layer re-extracted with DCM twice more. The combined organic fractions were dried with magnesium sulfate, filtered and evaporated to a crude. Purification by flash chromatography on SiO$_2$ eluting with dichloromethane methanol:880 NH$_3$ (97:3:0.3) afforded the desired product as a clear oil 4.5 g (21%) together with a further 10 g of partially purified material.

$^1$H NMR (DMSO-d6, 400 MHz) δ: 0.8 (t, 3H), 1.05 (bs, 3H), 1.4 (m, 1H), 2.95 (bs, 2H), 3.35 (bm, 3H), 4.6 (bs, 1H) LRMS (ESI+) m/z 240 (MNa$^+$)

EXAMPLE 57

(2S)-2-(propylamino)propan-1-ol hydrochloride

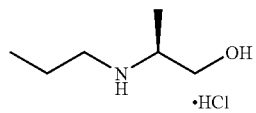

The pure material from example 56 (4.2 g, 0.021 mol) was dissolved in dioxan (10 mL) and treated with 4M HCl in dioxan (30 mL). The mixture was stirred at room temperature for 16 hours and then evaporated to a white solid (2.74 g, 92%)

$^1$H NMR (DMSO-d6, 400 MHz) δ: 0.9 (t, 3H), 1.15 (d, 3H), 1.6 (m, 2H), 2.8 (m, 2H), 3.15 (m, 1H), 3.5 (bm, 1H), 3.6 (m, 1H), 5.4 (bs, 1H), 8.8 (bd, 2H). LRMS (APCI+) 118 (MH$^+$)

EXAMPLE 58

(5S)-2-(3-methoxyphenyl-5-methyl-4-propylmorpholin-2-ol

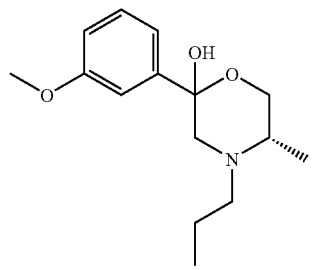

The product from example 57 (1.0 g, 6.6 mmol) was dissolved in toluene (10 mL) and treated with triethylamine (1.38 g, 14 mmol) before the addition of 2-bromo-3'-methoxyacetophenone (1.5 g, 6.6 mmol). The mixture was heated to 65° C. and stirred over 3 days. After cooling to room temperature the mixture was partitioned between brine and ethyl acetate, the organic layer separated, dried with magnesium sulfate, filtered and evaporated. The residue was purified by flash chromatography on SiO$_2$ eluting with ethyl acetate, to afford the desired morpholinol compound as a mixture of stereoisomers as a pale yellow oil (1.0 g 58%).

$^1$H NMR (DMSO-d6, 400 MHz) δ: 0.8 (m, 3H), 0.95 (d, 3H), 1.35 (m, 2H), 2.1 (m, 2H), 2.4 (bm, 1H), 2.6 (m, 1H), 2.75 (m, 1H), 3.5 (d, 1H), 3.75 (m, 4H), 6.0 (s, 0.75H), 6.1 (s, 0.25H), 6.85 (d, 1H), 7.05 (m, 2H), 7.25 (t, 1H). LRMS (ESI+) m/z 248 (M-H2O), 266 (MH$^+$), 288 (MNa+)

EXAMPLE 59

(5S)-2-(3-methoxyphenyl)-5-ethyl-4-propylmorpholine

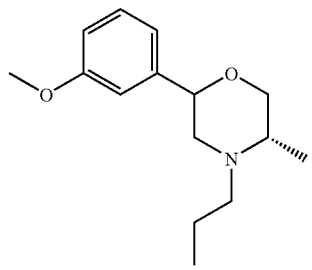

The product from example 58 (770 mg, 2.9 mmol) was dissolved in dichloromethane (20 mL) and cooled to −78° C. under a nitrogen atmosphere. Triethylsilane (3.7 mL, 23 mmol) was added to the stirred mixture followed by trimethylsilyltriflate (1.1 mL, 5.8 mmol). Stirring was continued overnight and the reaction mixture allowed to reach room temperature. The reaction was quenched by the addition of saturated aqueous sodium bicarbonate solution and extracted with dichloromethane (three times). The combined organic layers were dried with magnesium sulfate, filtered and evaporated. The crude product was purified by flash chromatography on SiO$_2$ dichloromethane:methanol:880 ammonia (97:3: 0.3): to yield the desired morpholine compound (600 mg, 83%)

$^1$H NMR (CDCl$_3$, 400 MHz) δ: 0.95 (m, 3H), 1.1 (b,d, 3H), 1.6 (bm, 2H), 2.2-3.1 (5H), 3.5 (bm, 1H), 4.85 (m, 4H), 4.6 (b, 1H), 6.8 (d, 1H), 6.95 (m: 2H), 7.25 (m, 1H+CHCl$_3$)

LRMS (APCI+) m/z 250 (MH$^+$)

Analysis found C, 71.53%; H, 9.21%; N, 5.55%. C$_{15}$H$_{23}$NO$_2$.0.15H$_2$O requires C, 71.48%; H, 9.32%; N, 5.56%.

EXAMPLE 60

3-[(5S)-5-methyl-4-propylmorpholin-2-yl]phenol

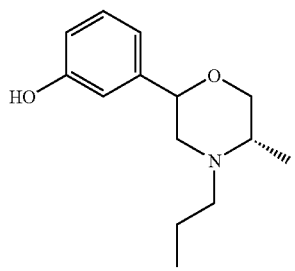

The material from example 59 (400 mg, 1.6 mmol) was dissolved in 48% aqueous hydrobromic acid (8 mL) and the mixture heated to 80° C. overnight. After cooling to room temperature, the mixture was quenched by the addition of saturated aqueous sodium bicarbonate, and the mixture extracted with dichloromethane (three times). The combined organic layers were dried with magnesium sulfate, filtered and evaporated to give the products as a white solid (285 mg, 76%)

¹H NMR (CDCl₃, 400 MHz) δ: 0.9 (m, 3H), 1.1+1.2 (2×d, 3H), 1.5 (m, 2H), 2.3 (m, 2H), 2.5 (bm, 1H), 2.8 (bm, 1H), 3.1 (d, 1H), 3.5 (bm, 1H), 3.85 (bm, 1H), 4.6 (d, 1H), 6.8 (m, 2H), 6.95 (m, 1H), 7.2 (t, 1H)

LRMS (APCI+), 236 (MH⁺)

Analysis found C, 70.61%; H, 9.00%; N, 5.86%. CO₁₄H₂₁NO₂.0.1H₂O requires C, 70.91%; H, 9.01%; N, 5.91%.

This mixture of diasteroisomers was separated on a Chiralcel OJ-H (250*21.2 mm) HPLC column. Mobile phase 100% MeOH, flow rate 15 ml/min.

Sample preparation 200 mg dissolved in 4 ml MeCH, 250 μL injection.

Two major peaks were obtained, with retention times 5.822 min (example 60A, 57 mg 28%) and 7.939 min (example 60B, 12 mg, 6%)

EXAMPLE 60A

¹H NMR (CDCl₃, 400 MHz) δ: 0.85 (t, 3H), 1.05 (d, 3H), 1.5 (m, 2H+ H₂O), 2.2 (m, 2H), 2.4 (m, 1H), 2.8 (m, 1H), 3.0 (d, 1H), 3.4 (t, 1H), 3.9 (dd, 1H), 4.55 (d, 1H), 5.6 (bs, 1H), 6.75 (d, 1H), 6.85 (s, 1H), 6.95 (d, 1H), 7.2 (t, 1H)

HRMS m/z 236.1643 (MH⁺)

EXAMPLE 60B

¹H NMR (CDCl₃, 400 MHz) δ: 0.95 (t, 3H), 1.15 (d, 3H), 1.55 (m, 2H), 2.4 (m, 2H), 2.55 (t, 1H), 2.65 (dd, 1H), 2.95 (bm, 1H), 3.8 (d, 1H), 3.95 (d, 1H), 4.55 (dd, 1H), 6.75 (d, 1H), 6.85 (s, 1H), 6.95 (d, 1H), 7.2 (t, 1H)

HRMS m/z 236.1643 (MH⁺)

EXAMPLE 61

(S)-2-propylamino-propan-1-ol hydrochloride

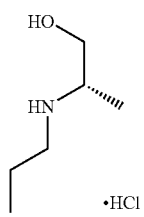

To (S)-(+)-2-amino-1-propanol (19.6 g, 0.26 mol) dissolved in dichloromethane (500 ml) was added propionaldehyde (20.9 ml, 0.28 mol) followed by pre-dried powdered 4 A molecular sieves (40 g) and the mixture stirred at room temperature overnight. The mixture was filtered through a pad of celite, the pad washed with dichloromethane, and solvent evaporated to give a clear oil. This oil was dissolved in methanol (200 ml) and NaBH₄ was added portionwise over 15 minutes. The mixture was stirred at room temperature overnight, then quenched by cautious addition of 2M HCl₍aq₎ (200 ml), basified by addition of 2M NaOH (200 ml) and methanol removed by evaporation. Di-tert-butyldicarbonate (115 g, 0.52 mol) was added followed by 1,4-dioxan (200 ml) and the mixture stirred at room temperature overnight. 1,4-dioxan was removed by evaporation giving a clear oil. To this oil was added 4M HCl in 1,4-dioxan (200 ml) and the mixture stirred at room temperature overnight. The solvent was removed by evaporation to give a white solid (24 g).

¹H NMR (DMSO, 400 MHz) δ: 0.95 (t, 3H), 1.2 (d, 3H), 1.6 (m, 2H), 2.8 (m, 2H), 3.15 (m, 1H), 3.5 (bm, 1H), 3.6 (m, 1H), 5.4 (b, 1H), 8.6-8.9 (bd, 2H) LRMS (APCI+), 118 (MH⁺)

EXAMPLE 62

(5S)-4-propyl-5-methylmorpholin-2-one

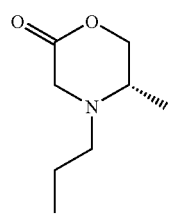

The material from example 61 (4 g, 26 mmol) was dissolved in benzene, followed by the addition of N-ethyldiisopropylamine (9.07 ml, 52 mmol) and methyl bromoacetate (2.4 ml, 26 mmol). The mixture was heated to reflux with azeotropic removal of water overnight. The solvent was removed by evaporation, the crude material dissolved in methanol, pre-absorbed onto SiO₂ and flash chromatographed on SiO₂ eluting with 40% EtOAc/Pentane to afford the title morpholinone as a clear oil (1.78 g).

¹H NMR (CDCl₃, 400 MHz) δ: 0.9 (t, 3H), 1.1 (d, 3H), 1.5 (m, 2H), 2.25 (m, 1H), 2.6 (m, 1H), 2.8 (m, 1H), 3.2 (d, 1H), 3.6 (d, 1H), 4.05 (dd, 1H), 4.3 (dd, 1H)

t.l.c. Rf=0.18 (50% EtOAc/Pentane, UV visualisation)

EXAMPLE 63

(5S)-2-[6-(2,5-dimethyl-1H-pyrrol-1-yl)-pyridin-3-yl]-4-propyl-5-methylmorpholin-2-ol

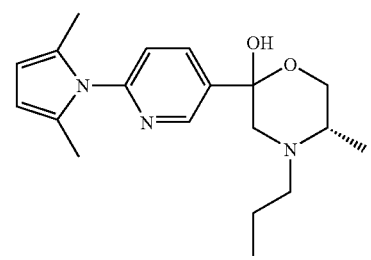

5-bromo-2-(2,5-dimethyl-pyrrol-1-yl)-pyridine (1.5 g 5.9 mmol) was azeotroped with toluene and dissolved in THF (20 ml). This mixture was cooled to −78 C. and t-butyllithium (1.7M in pentane, 7 ml, 11.9 mmol) was added maintaining the temperature below −70 C. The material from example 62 was dissolved in THF (20 ml) and added to the mixture immediately on completion of the t-butyllithium addition. The mixture was allowed to stir at −78° C. for 30 minutes at which time NH₄Cl (10% aq, 150 ml) was added and the mixture extracted into EtOAc (200 ml), dried with magnesium sulphate, filtered and evaporated. Flash chromatography on SiO₂ eluting with a stepped gradient from 25% EtOAc/pentane to 50% EtOAc/pentane gave the title compound as mixture of diastereoisomers in approximately 3.5:1 ratio as a yellow oil (480 mg).

¹H NMR (CDCl₃, 400 MHz) (diastereomers) δ: 0.95 (m, 3H), 1.1, 1.2 (2×d, 3H) 1.5 (m, 2H), 2.15 (s, 6H), 2.4 (m, 1H), 2.5 (d, 1H), 2.6 (m, 1H), 2.75 (m, 1H), 3.85-3.95 (m, 1H), 3.6, 3.75, 4.4 (3×m, 2H), 5.15 (bs, 1H), 5.9 (s, 2H), 7.2 (d, 1H), 8.05 (dd, 1H), 8.8 (s, 1H)

LRMS (ES+), 330 (MH+), 352 (MNa+)
LRMS (ES-), 328 (M-H)

EXAMPLE 64

(2S)-2-[{(2RS)-2-[6-(2,5-dimethyl-1H-pyrrol-1-yl)pyridin-3-yl]-2-hydroxyethyl}propyl)amino]propan-1-ol

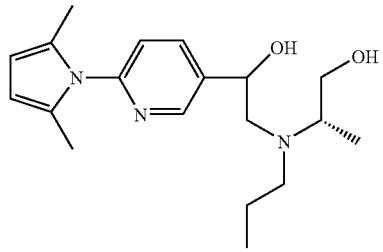

(5S)-2-[6-(2,5-dimethyl-1H-pyrrol-1H-yl)pyridin-3-yl]-4-propyl-5-methylmorpholin-2-ol (480 mg 1.45 mmol) was dissolved in ethanol (5 mL) and water (2 mL) and treated with sodium borohydride (220 mg, 5.8 mmol). The reaction mixture was left stirring overnight at room temperature before being quenched by the addition of saturated aqueous NH₄Cl (50 mL) and extracted with ethyl acetate (2×100 mL). The organic extracts were combined, dried with MgSO₄ and evaporated to give 400 mg of a fluffy white solid which was used without further purification ¹H NMR (CDCl₃, 400 MHz) diastereomers δ: 0.8-1.1 (m, 6H), 1.15, 1.35 (2×d, 3H), 1.6-2.0 (m, 2H), 2.1 (s, 6H), 2.5-4.05 (m, 7H), 4.8-5.2 (m, 1H), 5.9 (s, 2H), 7.2 (m, 1H), 7.8-8.1 (m, 1H), 8.55 (m, 1H).

LRMS (ES+), 332 (MH+)

EXAMPLE 65

(2S)-2-[[(2RS)-2-(6-aminopyridin-3-yl)-2-hydroxyethyl](propyl)amino]propan-1-ol

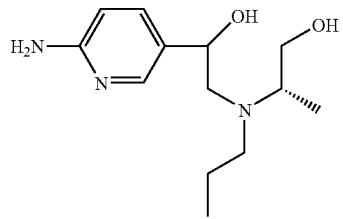

(2S)-2-[[(2RS)-2-(6-aminopyridin-3-yl)-2-hydroxyethyl](propyl)amino]propan-1-ol (400 mg, 1.2 mmol) was dissolved in EtOH (5 mL), hydroxylamine hydrochloride (419 mg, 6 mmol) was added and the mixture heated to 80° C. overnight. The solvent was removed under vacuum and the residue purified by flash chromatography on SiO₂ eluting with dichloromethane/methanol/880 ammonia (95:5:0.5 increasing polarity to 93:7:1) to afford the title compounds as a mixture of diastereoisomers (300 mg, 98%)

¹H NMR (CDCl₃, 400 MHz) (2 diastereomers) δ: 0.82-0.97 (6H, m), 2.40-2.77 (2H, m), 3.27-3.51 (2H, m), 4.51 (1H, m), 6.58 (1H, m), 7.49 (1H, m), 7.86 (1H, m)

LRMS (APCI+), 254 (MH+)

EXAMPLES 66 AND 67

5-[(2S,5S)-5-methyl-4-propylmorpholin-2-yl]pyridin-2-amine and 5-[(2R,5S)-5-methyl-4-propylmorpholin-2-yl]pyridin-2-amine

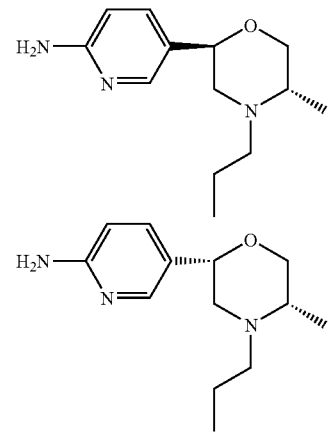

The "diol" from example 65 (300 mg, 1.2 mmol) was dissolved in dichloromethane (3 mL), and concentrated sulphuric acid (3 mL) was added. The mixture was stirred at room temperature for 3 hours. The reaction was cooled to 0° C., quenched by the cautious addition of 6M sodium hydroxide solution and then extracted with dichloromethane (4×50 mL). The combined extracts were dried (MgSO₄) and evaporated to a brown gummy solid. Purification by flash chromatography on SiO₂ eluting with 10% methanol in ethyl acetate afforded 5 mg of material enriched in the less polar diastereomer (ca. 80% d.e.), 12 mg of material enriched in the less polar diastereomer (ca. 80% d.e.) and 150 mg of material ca. 1:1 mixture of diastereoisomers (total yield 167 mg, 59%). The latter 1:1 mixture was subjected to purification by HPLC using a Chiralpak OD-H column (250×21.2 mm), eluting with methanol/ethanol (1:1).

The faster eluting diastereoisomer (retention time 8.1 min) was obtained in >99% d.e (60 mg, 21%). ¹H NMR (CDCl₃, 400 MHz) 0.88 (3H, t), 1.01 (3H, d), 1.26 (3H, t), 1.37-1.58 (2H, m), 2.18-2.28 (2H, m), 2.36-2.47 (1H, m), 2.69-2.77 (1H, m), 2.90 (1H, m), 3.38 (1H, m), 3.72 (2H, d), 3.82 (1H, m), 4.40 (2H, brs), 4.45 (1H, dd), 6.48 (1H, d), 7.45 (1H, dd), 8.04 (1H, d)

LRMS (ES+): m/z 236 (MH+)
$[\alpha]_D^{25}$ 46.28 (c 0.13, MeOH)

The slower eluting diastereoisomer (retention time 10.5 min) was obtained in >99% d.e. (62 mg, 22%). ¹H NMR (CDCl₃, 400 MHz) 0.93 (3H, t), 1.11 (3H, d), 1.49 (2H, m), 2.38 (2H, m), 2.50-2.56 (2H, m), 2.89 (1H, m), 3.75 (1H, m), 3.89 (1H, m), 4.40 (2H, brs), 4.46 (1H, m), 6.50 (1H, d), 7.50 (1H, dd), 8.07 (1H, d)

LRMS (ES+): m/z 236 (MH+)
$[\alpha]_D^{25}$ 22.58 (c 0.13, MeOH)

The invention claimed is:

1. A method of treating female sexual dysfunction, male erectile dysfunction or neurodegeneration comprising administering a therapeutically effective amount of the compound

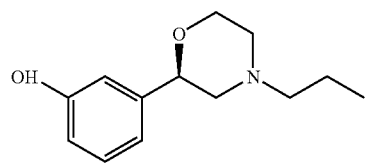

or a pharmaceutically acceptable salt thereof, to a patient in need of treatment thereof.

2. A method of treating male erectile dysfunction comprising administering a therapeutically effective amount of the compound

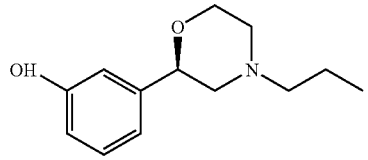

or a pharmaceutically acceptable salt thereof, to a patient in need of treatment thereof.

3. A method of treating sexual arousal disorder, orgasmic disorder or sexual pain disorder in females comprising administering a therapeutically effective amount of the compound

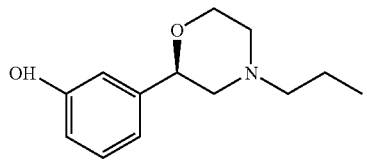

or a pharmaceutically acceptable salt thereof, to a patient in need of treatment thereof.

* * * * *